Figure 1:
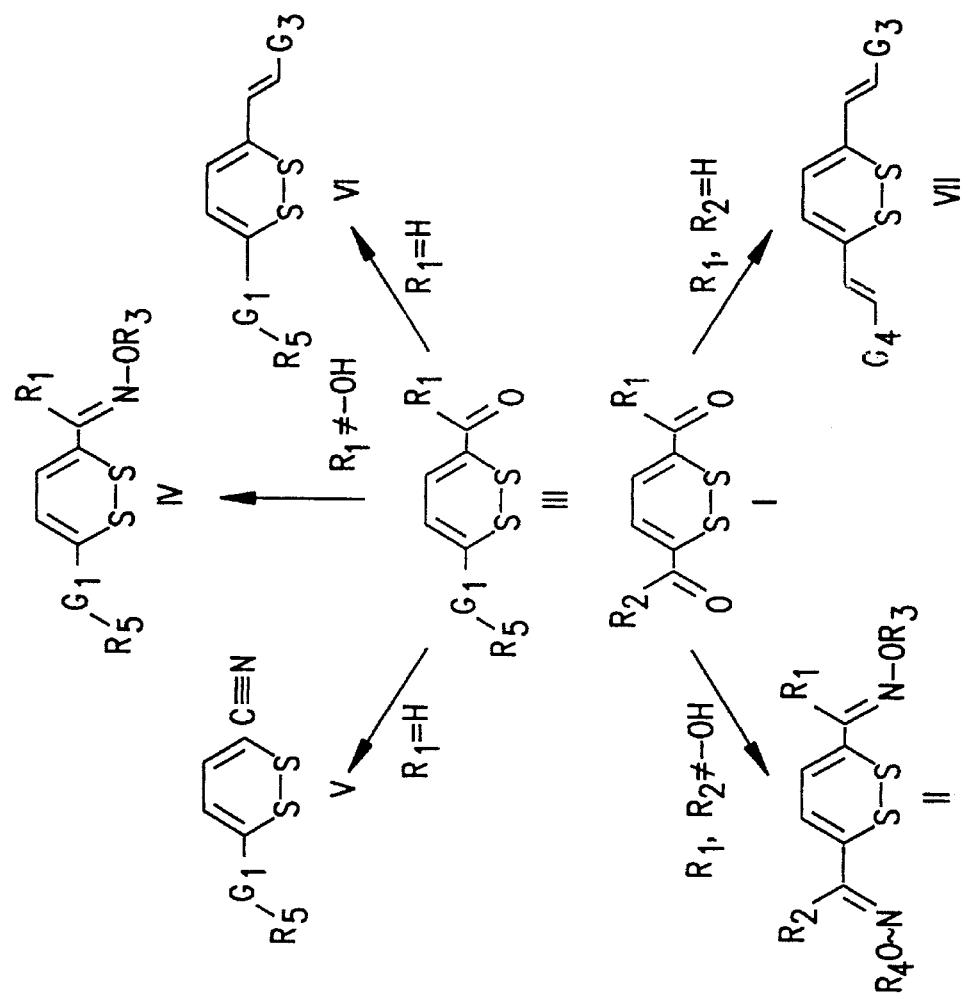

United States Patent [19]

Bierer et al.

[11] Patent Number: 5,580,897
[45] Date of Patent: Dec. 3, 1996

[54] 1,2-DITHIINS HAVING ANTIFUNGAL ACTIVITY

[75] Inventors: Donald E. Bierer, Daly City; Patricia Peterli-Roth, Hayward, both of Calif.

[73] Assignee: Shaman Pharmaceuticals, Inc., San Francisco, Calif.

[21] Appl. No.: 396,449

[22] Filed: Feb. 28, 1995

Related U.S. Application Data

[63] Continuation-in-part of Ser. No. 212,096, Mar. 11, 1994.
[51] Int. Cl.$^6$ ........................ C07D 339/08; A61K 31/385
[52] U.S. Cl. ............................. 514/436; 549/20; 549/22
[58] Field of Search ........................ 549/20, 22; 514/436

[56] References Cited

U.S. PATENT DOCUMENTS

| 4,659,733 | 4/1987 | DuPriest et al. | 514/436 |
| 5,202,348 | 4/1993 | Towers et al. | 514/436 |
| 5,453,500 | 9/1995 | Koreeda et al. | 536/123 |

FOREIGN PATENT DOCUMENTS

| 2118437 | 10/1972 | Germany . | |
| WO95/05817 | 3/1995 | WIPO | 514/436 |

OTHER PUBLICATIONS

Mao et al., "In vitro Evaluation of a Series of Novel Substituted 1,2–Dithiins", XII Congress of the International Society for Human and Animal Mycology, Adelaide, South Australia, Mar. 13–18, 1994.
Koreeda and Yang, "Chemistry of 1,2–Dithiins. Synthesis of the Potent Antibiotic Thiarubrine A", J Am Chem Soc 116:10793–10794, 1994.
Koreeda and Yang, "The Chemistry of 1,2–Dithiins: Synthesis of the 1,2–Dithiin and and 3,6– Disubstituted 1,2–Dithiins", Synlett 201–203, Mar. 1994.
Block et al., 1994, "Total Synthesis of Thiarubrine B [3–(3–Buten–1–ynyl)–6–(1,3–pentadiynyl)–1,2–dithiin], the Antibiotic Principle of Giant Ragweed (*Ambrosia trifida*)", J Am Chem Soc 116:9403–9404.
Freeman et al., 1993, "Naturally Occurring 1,2–Dithiins" in Reviews on Heteroatom Chemistry; Oae, S., Ed., Tokyo pp. 1–19.
Hudson et al., 1993, "Light–Mediated Activities of Thiarubrines Against Human Immunodeficiency Virus", Photochemistry and Photobiology 57:675–680.
Yang and Koreeda, 1993, American Chemical Society, Division of Organic Chemistry, 206th National Meeting, Aug. 22–27 1993, Abstract 349.
Ellis et al., 1993, "A Diathiacyclohexadine Polyyne Alcohol from *Ambrosia Chamissonis*", Phytochemistry 33:224–228.
Gomez–Barrios et al., 1992, "Studies on the Biosynthesis of Thiarubrine A in Hairy Root Cultures of *Ambrosia Artemisiifolia* Using $^{13}$C–Labelled Acetates", Phytochemistry 31:2703–2707.
Cimiragilia et al., 1991, "An AB Initio Study of the Structure and Electronic Spectrum of 1,2–Dithiete and 1,2–Dithiin", J Mol Struct (Therochem). 230:287–293.

Greene and Wuts, "Protective Groups in Organic Synthesis", John Wiley & Sons, Inc., New York, 1991, P. 296.
Aihara et al., 1990, "Chemical Evolution, Biosynthesis, and Aromaticity", J Bull Chem Soc Jpn, 63:2899–2903.
Balza et al., 1990, "Dithiacyclohexadine Chlorohydrins and Related Sulphur Containing Polyynes from *Ambrosia Chamissonis*", Phytochemistry 29:2901–2904.
Balza et al., 1989, "Dithiacyclohexadienes and Thiophenes from *Ambrosia Chamissonis*", Phytochemistry 28(12):3523–3524.
Constabel et al., 1989, "Incorporation of $^{35}$S into Dithiacyclohexadiene and Thiophene Polyines in Hairy Root Cultures of *Chaenactis Douglasii*", Phytochemistry 28:93–95.
Freeman et al., 1989, "The Chemistry of 1,2–Dithiins", Sulfur Reports 9(3):207–256.
Constabel et al., 1989, "The Complex Nature of the Mechanism of Toxicity of Antibiotic Dithiacyclohexadiene Polyines (Thiarubrines) from the Asteraceae", Planta Med 55:35–37.
Hudson et al., 1986, "Comparison of the Antiviral Effects of Naturally Occurring Thiophenes and Polyacetylenes", N Planta Medica 52:453–457.
Hudson et al., 1986, "Antiviral Properties of Thiarubrine–A, a Naturally Occurring Polyine", Planta Med 52:51–54.
Cosio et al., 1986, "Production of Antibiotic Thiarubrines by a Crown gall Tumor Line of *Chaenactis douglasii*", J Plant Physiol 124:155–164.
Towers et al., 1985, "Antibiotic Properties of Thiarubrine A, a Naturally Occurring Dithiacyclohexadine Polyine", Planta Medica 51:225–229.
Rodriguez et al., 1985, "Thiarubrine A, a Bioactive Constituent of *Aspilia* (Asteraceae) Consumed by Wild Chimpazees", N Experimenta 41:419–420.

(List continued on next page.)

*Primary Examiner*—Zinna Northington-Davis
*Attorney, Agent, or Firm*—Pennie & Edmonds

[57] ABSTRACT

Novel 1,2-dithiin compounds useful as antifungal or anti-infective agents, as well as methods for their use as such, are described. The 1,2-dithiin compounds are particularly effective in treating infections, especially those caused by *Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, Histoplasma capsulatum*, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdlovirus, Togavirus, Hepadnavirus, *Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis, Streptococcus pyogenes; Straptococcus pneumonia, Viridans streptococci, Haemophilus influenzae, Proteus mirabilis, proteus vulgaris* and *Bacterioides fragilis*.

28 Claims, 1 Drawing Sheet

OTHER PUBLICATIONS

Kokwaro, 1976, Medicinal Plants of East Africa, East African Literature Bureau, pp. 58–76.

Ried and Ochs, 1972, "Electrophilic Addition of Disulfur Dichloride (S2C12 to Alkynes", Chemical Abstracts 77:433, Abstract 4826m.

Schroth et al., 1967, "1,2–Dithiins, a New Type of Heterocycle", Angew Chem, Int Ed Eng 6:698–699.

Schroth et al., 1966, "Stereoisomeric 1,4–dimercaptobutadiene", Chemical Abstracts vol. 64, Abstract 3339a.

Bohlmann and Kleine, 1965, "Uber rote Naturliche Schwefelacetylenverbindungen", M Chem Ber 98:3081–3086.

Mortensen et al., 1964, "Studies Related to Naturally Occuring Acetylene Compounds", Acta Chem Scand 18:2392–2394.

Dzhemilev et al., 1986, "A new catalytic reaction of elemental sulfur with acetylenes by the action of cobalt complexes", *Izv. Akad. Nauk SSSR, Ser. Khim.* 5:1211–1212.

Dzhemilev et al., 1987, "An original method for the preparation of sulfides and disulfides involving cobalt complexes", *Izv. Akad. Nauk SSSR, Ser. Khim.* 8:1918.

Koreeda et al, Syn Lett, Mar. 1994, pp. 201–203.

Fabian, Collection, Czechoslovak Chem. Communication, vol. 53, No. 9, Sep. 1988, pp. 2096–2115.

1,2-DITHIINS HAVING ANTIFUNGAL ACTIVITY

The present application is a continuation-in-part of copending application Ser. No. 08/212,096 filed Mar. 11, 1994, now pending, which is incorporated herein by reference in its entirety.

1. FIELD OF THE INVENTION

This invention pertains to a novel group of 1,2-dithiin compounds and their use as antifungal or anti-infective agents.

2. BACKGROUND OF THE INVENTION 1,2-Dithiins are six-membered antiaromatic heterocycles having a disulfide linkage in place of the two contiguous CH groups of benzene. [Cimiraglia, R.; Fabian, J.; Hess, B. A., Jr. *J. Mol. Struct.* (Therochem) 1991, 230, 287–293; Aihara, *J. Bull. Chem. Soc.* Jpn. 1990, 63, 2899–2903]. The 1,2-dithiin class of heterocycles have been of interest due to their interesting physical and biological properties. Ten natural products containing this unique heterocycle have been isolated since the 1960's, primarily from plants of the family Asteraceae (Mortensen, J. T., Sorensen, J. S., Sorensen, N. A.; *Acta Chem. Scand.* 1964, 18, 2392–2394; Bohlmann, F. Klein, K., *M. Chem. Ber.* 1965, 98, 3081–3086; Kokwaro, J. O., Medicinal Plants of East Africa; East African Literature Bureau, Nairobi, Kenya: 1976, pgs. 58–76; Rodriguez, E.; Aregullin, M.; Nishida, T.; Uehara, S.; Wrangham, R. W.; Abramowski, Z.; Finlayson, A. J.; Towers, G. H. N. *Experimentia*, 1985, 41, 419–420.; Gomez-Barrios, M. L.; Parodi, F. J.; Vargas, D.; Quijano, L; Hjortso, M. A.; Flores, H. E.; Fisher, N. H. *Phytochemistry,*, 1992, 31, 2703–2707; Constabel, C. P.; Towers, G. H. *N. Phytochemistry*, 1989, 28, 93–95). Among these natural products is thiarubrine A, which was isolated from leaves of *Aspilia mossambicesis* and *Aspilia plurisetta*, (Rodriquez, E.; Aregullin, M.; Nishida, T.; Uehara, S.; Wrangham, R. W.; Abramowski, Z.; Finlayson, A. J.; Towers, G. H. N., *Experimentia*, 1985, 41, 419–420), from the roots of *Chaenactis douglasii* and *Ambrosia chamissonis* (Ellis, S.; Balza, F.; Towers, G. H. N. *Phytochemistry*, 1993, 33, 224–228 Balza, F.; Towers, G. H. N. *Phytochemistry*, 1990, 29, 2901–2904) and from the roots of *Ambrosia artemisiifolia* (Gomez-Barrios, M. L.; Parodi, F. J.; Vargas, D.; Quijaro, L.; Hjortso, M. A.; Flores, H. E.; Fischer, N. H., *Phytochemistry*, 1992, 31, 2703–2707). Thiarubrine A has been shown to possess both antifungal and antiviral activity but is also cytotoxic (Constabel, C. P.; Towers, G. H. N., *Planta Med.*, 1989, 55, 35–37; Towers, G. H. N.; Abramowski, Z.; Finlayson, A. J.; Zucconi, A., *Planta Med.*, 1985, 51, 225–229; Hudson, J. B.; Graham, E. A.; Fong, R.; Finlayson, A. G.; Towers, G. H. N., *Planta Med.*, 1986, 52, 51–54). Other thiarubrines which possess antifungal and antibacterial activity have been described (Towers, G. H. N.; Bruening, R. C. B.; Balza, F.; Abramowski, Z. A.; Lopez-Bazzochi, I. U.S. Pat. No. 5,202,348, Apr. 13, 1993; Balza, F.; Towers, G. H. N., *Phytochemistry*, 1990, 29, 2901–2904). Such compounds are both heat and light sensitive, and easily convertible to their corresponding thiophenes under proper thermal or photochemical conditions. All of the natural products possess acetylenic sidechains in the 3- and 6-positions of the dithiin, which may in part account for their instability. Additionally, compounds related to dithiins have been known to possess antiviral, antibacterial, and antifungal activities (Hudson, J. R.; Graham, E. A.; Chan, G.; Finlayson, A. J.; Towers, G. H. N. *Planta Med.* 1986, 52, 453–457; Cosio, E. G.; Norton, R. N.; Towers, E.; Finlayson, A. J.; Rodriguez, E.; Towers, G. H. N. *J. Plant Physiol.* 1986, 124, 155–164). Naturally occurring 1,2-dithiins have also been isolated from the roots and leaves of *Chaenactis douglasii*, root cultures of *Eriophyllum lanatum, Rudbeckia hirta, Ambrosia chamissonis, Aspilia mossambicensis, Aspilia pluriseta, Aspilia rudis,* and other species of Asteraceae (Freeman, F.; Aregullin, M.; Rodriguez, E. "Naturally Occurring 1,2-Dithiins" in Reviews on Heteroatom Chemistry; Oae, S., Ed., MYU: Tokyo 1993; vol. 9, pp. 1–19; Freeman, F.; Kim, D. S. H. L.; Rodriquez, E. "The Chemistry of 1,2-Dithiins" in Sulfur Reports; Senning, A. Ed., Langhorne, Pa. 1989; vol 9, pp. 207–256). In addition to the observed antifungal, antiviral, antibacterial, and cytotoxic activities which the natural 1,2-dithiins (thiarubrines) possess, some naturally occuring 1,2-dithiins have been shown to possess light mediated antiviral activity against the human immunodeficiency virus (Hudson, J. B.; Balza, F.; Harris, L.; Towers, G. H. N. Photochem. and Photobiol. 1993, 57, 675–680), and nematocidal activity and antitumor properties (Freeman, F.; Aregullin, M.; and Rodriguez, E. "Naturally Occurring 1,2-Dithiins" in Reviews on Heteroatom Chemistry, Oae, S., Ed., MYU: Tokyo, 1993; vol. 9, pp. 1–19.

The total synthesis of two naturally occurring 1,2-dithiins (thiarubrine A and thiarubrine B) have been reported (Block, E.; Guo, C.; Thiruvazhi, M.; Toscano, P. J., *J. Am. Chem. Soc.* 1994, 116, 9403; Koreeda, M.; Yang, W., *J. Am. Chem. Soc.*, 1994, 116, 10793–10794). Abstract 349 of W. Wang and M. Koreeda, American Chemical, Society, Division of Organic Chemistry, 206th National Meeting, Aug. 22–27, 1993 describes the synthesis of 1,2-dithiins from regioselective bisaddition of benzylthiol to 1,4-disubstituted diynes. Abstract of Mao et al., XII Congress of the International Society for Human and Animal Mycology, Adelaide, South Austrailia, March 13–18, 1994, describes synthetic mono and diester dithiin derivatives having fungicidal activity.

The preparation of 1,2-dithiin and its 3,6-disubstituted analogs have been reported (Schroth, W.; Billig, F.; Reinhold, G. *Angew. Chem., Int. Ed. Engl.* 1967, 6, 698–699). The synthesis of certain 1,2-dithiin analogs has further been described (M. Koreeda and W. Yang, Synlett, 1994, 201–203).

Citation or identification of any reference in Section 2 of this application shall not be construed as an admission that such reference is available prior art to the invention.

Due to the natural products' inherent cytotoxicity and extreme instability to light, these substances have obvious disadvantages for use as therapeutic agents. Thus there is a need for antifungal agents which are neither inherently cytotoxic nor extremely unstable to light.

To the knowledge of the inventors, no prior study has described any antifungal or anti infective activity of 1,2-dithiin compounds lacking acetylenic, mono or diester moieties, nor has there been any suggestion in the prior art that such compounds of the present invention would be useful as such.

3. SUMMARY OF THE INVENTION

The present invention provides novel 1,2-dithiin compounds, as well as pharmaceutically acceptable salts thereof, having antifungal or anti-infective activity, pharmaceutical compositions comprising the novel 1,2-dithiin compounds of the present invention, as well as methods for their use. Particularly, the invention provides 1,2-dithiin compounds having the formula I:

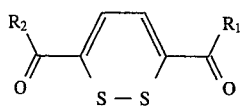

and pharmaceutically acceptable salts thereof, wherein:

$R_1$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl; and $R_2$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl, with the proviso that $R_1$ and $R_2$ are not simultaneously hydrogen.

The novel 1,2-dithiin compounds of formula I are useful as antifungal or anti-infective agents.

The invention further provides 1,2-dithiin derivatives having the formula II:

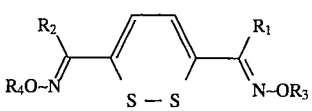

and pharmaceutically acceptable salts thereof, wherein:

$R_1$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_2$ is selected from the group consisting of hydrogen, —OH, a $C_2$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_3$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

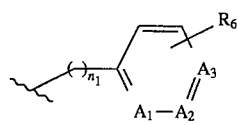

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_1$, $A_2$, and $A_3$ are independently N, or C—H;

$R_6$ is selected from the group consisting of hydrogen, —OH, halogen, —OCH$_3$, —SH, —S(O)n$_2$CH$_3$, and —NH$_2$;

$n_1$=0–2;

$n_2$=0–2;

$R_4$ is selected from the group consisting of hydrogen, a $C_2$–$C_{10}$ alkyl group, a $C_2$–$C_{10}$ alkenyl group, a $C_2$–$C_{10}$ alkynyl group, phenyl, benzyl and a heteroaromatic radical of the type:

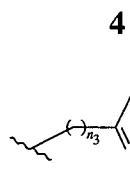

said $C_2$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, —OH, halogen, —OCH$_3$, —SH, —S(O)n$_4$CH$_3$, and —NH$_2$;

$n_3$=0–2

$n_4$=0–2; and with the proviso that $R_1$ and $R_2$ are not simultaneously —OH.

The novel 1,2-dithiin compounds of formula II are useful as antifungal or anti-infective agents. It will be understood that the 1,2-dithiin derivatives having the formula II comprise those wherein $R_4$O and $R_2$ are in both the cis and trans configuration and $R_3$O and $R_1$ are in both the cis and trans configuration.

The invention further provides novel 1,2-dithiin derivatives having the formula III:

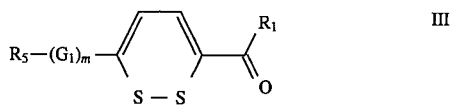

and pharmaceutically acceptable salts thereof, wherein:

$R_1$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$G_1$ is selected from the group consisting of a $C_2$–$C_{10}$ alkyl or branched alkyl group and a $C_3$–$C_{10}$ cycloalkyl group;

m=0–1;

$R_5$ is selected from the group consisting of hydrogen, azido, cyano, formyl, halogen, OR$_{10}$, SR$_{11}$, COR$_{12}$, CR$_2$(=NOR$_4$) and CO$_2$R$_{13}$;

$R_{10}$ is selected from the group consisting of hydrogen, a $C_1$–$C_{10}$ alkyl group, a $C_3$–$C_{10}$ cycloalkyl group, an acyl radical of the type

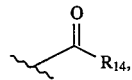

phenyl, benzyl and a 5–6 membered heteroaryl ring; said phenyl, benzyl and 5–6 membered heteroaryl ring being optionally substituted with one or more halogen, SCH$_3$, COOH, COOCH$_3$, OH, COOCH$_2$CH$_3$, OCH$_3$, OCH$_2$CH$_3$, NO$_2$, CF$_3$, $C_1$–$C_6$ alkyl, NH$_2$, and OAc;

$R_{14}$ is selected from the group consisting of methyl, ethyl, 1-(methyl)ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and a 5–6 membered ring heteroaryl radical being optionally substituted with one or more halogen, SCH$_3$, COOH, COOCH$_3$, COOCH$_2$CH$_3$, OH, OAc, OCH$_3$, OCH$_2$CH$_3$, NO$_2$, CF$_3$, $C_1$–$C_6$ alkyl and NH$_2$;

$R_{11}$ is selected from the group consisting of hydrogen, a $C_1$–$C_{10}$ alkyl group, a $C_3$–$C_{10}$ cycloalkyl group, an acyl radical of the type

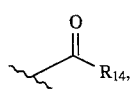

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{12}$ is selected from the group consisting of methyl, ethyl, 1-(methyl)ethyl; n-propyl, an alkyl radical of 4 to 10 carbon atoms, a $C_3$–$C_8$ cycloalkyl group, phenyl and benzyl; said phenyl and benzyl groups being optionally substituted with one or more halogen, $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$; and $R_{13}$ is selected from the group consisting of hydrogen, methyl, ethyl, 1-(methyl)ethyl, n-propyl, an alkyl radical of 4 to 10 carbon atoms, a $C_3$–$C_8$ cycloalkyl group, phenyl and benzyl; said phenyl and benzyl groups being optionally substituted with one or more $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl, $NH_2$ and halogen;

with the proviso that when m=0, $R_5$ is selected from the group consisting of cyano, formyl, $COR_{12}$, $CO_2R_{13}$, and $CR_2(=NOR_4)$, except that when $R_1$ is hydrogen and m=0, $R_5$ is not formyl;

wherein $R_2$ is selected from the group consisting of hydrogen, —OH, a $C_2$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

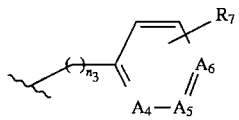

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, —OH, halogen, —$OCH_3$, —SH, —$S(O)n_4CH_3$, and —$NH_2$;

$n_3$=0–2; and $n_4$=0–2.

The novel 1,2-dithiin compounds of formula III are useful as antifungal or anti-infective agents.

The invention still further provides novel 1,2-dithiin derivatives having the formula IV:

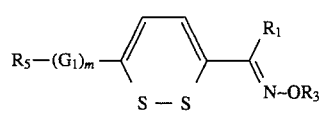

and pharmaceutically acceptable salts thereof, wherein:

$R_1$ is selected from the group consisting of hydrogen, a $C_2$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_3$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

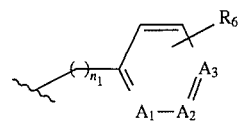

said $C_2$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_1$, $A_2$, and $A_3$ are independently N, or C—H;

$R_6$ is selected from the group consisting of hydrogen, —OH, halogen, —$OCH_3$, —SH, —$S(O)n_2CH_3$, and —$NH_2$;

$n_1$=0–2;

$n_2$=0–2;

$G_1$ is selected from the group consisting of a $C_2$–$C_{10}$ alkyl or branched alkyl group and a $C_3$–$C_{10}$ cycloalkyl group;

m=0–1;

$R_5$ is selected from the group consisting of hydrogen, azido, cyano, formyl, halogen, $OR_{10}$, $SR_{11}$, $COR_{12}$, $CR_2(=NOR_4)$ and $CO_2R_{13}$;

$R_{10}$ is selected from the group consisting of hydrogen, a $C_1$–$C_{10}$ alkyl group, a $C_3$–$C_{10}$ cycloalkyl group, an acyl radical of the type

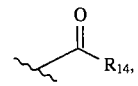

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, OH, $COOCH_2CH_3$, $OCH_3$, $OCH_2CH_3$, $NO_2$, $CF_3$, $C_1$–$C_6$ alkyl, $NH_2$, and OAc;

$R_{14}$ is selected from the group consisting of methyl, ethyl, 1-(methyl)ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and 5–6 membered ring heteroaryl radical being optionally substituted with one or more $SCH_3$, COOH, halogen, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{11}$ is selected from the group consisting of hydrogen, a $C_1$–$C_{10}$ alkyl group, a $C_3$–$C_{10}$ cycloalkyl group, an acyl radical of the type

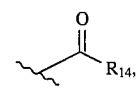

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{12}$ is selected from the group consisting of methyl, ethyl, 1-(methyl)ethyl; n-propyl, an alkyl radical of 4 to 10 carbon atoms, a $C_3$–$C_8$ cycloalkyl group, phenyl and benzyl; said phenyl and benzyl groups being optionally substituted with one or more $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$, and halogen;

$R_{13}$ is selected from the group consisting of hydrogen, methyl, ethyl, 1-(methyl)ethyl, n-propyl, an alkyl radical of 4 to 10 carbon atoms, a $C_3$–$C_8$ cycloalkyl group, phenyl and benzyl; said phenyl and benzyl groups being optionally substituted with one or more halogen, $SCH_3$, COOH, $COOCH_3$, $COOCH_2CH_3$, OH, OAc, $OCH_3$, $OCH_2CH_3$, $NO_2$, $NH_2$, $CF_3$ and $C_1$–$C_6$ alkyl;

with the proviso that when m=0, $R_5$ is selected from the group consisting of cyano, formyl, $COR_{12}$, $CO_2R_{13}$, and $CR_2(=NOR_4)$, wherein $R_2$ is selected from the group consisting of hydrogen, —OH, a $C_2$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_2$–$C_{10}$ alkyl group, a $C_2$–$C_{10}$ alkenyl group, a $C_2$–$C_{10}$ alkynyl group, phenyl, benzyl and a heteroaromatic radical of the type:

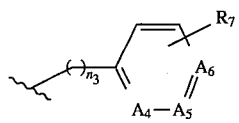

said $C_2$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, halogen, —OH, —$OCH_3$, —SH, —$S(O)n_4CH_3$, and —$NH_2$; and $n_3$=0–2; and $n_4$=0–2.

The novel 1,2-dithiin compounds of formula IV are useful as antifungal or anti-infective agents. It is to be understood that the 1,2-dithiin derivatives having the formula IV comprise those wherein $R_3O$ and $R_1$ are in both the cis and trans configuration.

The invention still further provides novel 1,2-dithiin derivatives having the formula V:

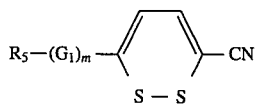

and pharmaceutically acceptable salts thereof, wherein:

$G_1$ is selected from the group consisting of a $C_2$–$C_{10}$ alkyl or branched alkyl group and a $C_3$–$C_{10}$ cycloalkyl group; m=0–1;

$R_5$ is selected from the group consisting of hydrogen, azido, cyano, formyl, halogen, $OR_{10}$, $SR_{11}$, $COR_{12}$, $CR_2(=NOR_4)$ and $CO_2R_{13}$;

$R_{10}$ is selected from the group consisting of hydrogen, a $C_1$–$C_{10}$ alkyl group, a $C_3$–$C_{10}$ cycloalkyl group, an acyl radical of the type

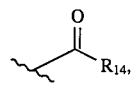

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, OH, $COOCH_2CH_3$, $OCH_3$, $OCH_2CH_3$, $NO_2$, $CF_3$, $C_1$–$C_6$ alkyl, $NH_2$, and OAc;

$R_{14}$ is selected from the group consisting of methyl, ethyl, 1-(methyl)ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and a 5–6 membered ring heteroaryl radical being optionally substituted with one or more $SCH_3$, COOH, halogen, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{11}$ is selected from the group consisting of hydrogen, a $C_1$–$C_{10}$ alkyl group, a $C_3$–$C_{10}$ cycloalkyl group, an acyl radical of the type

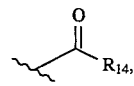

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{12}$ is selected from the group consisting of methyl, ethyl, 1-(methyl)ethyl; n-propyl, an alkyl radical of 4 to 10 carbon atoms, a $C_3$–$C_8$ cycloalkyl group, phenyl and benzyl; said phenyl and benzyl groups being optionally substituted with one or more $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$, halogen; and $R_{13}$ is selected from the group consisting of hydrogen, methyl, ethyl, 1-(methyl)ethyl, n-propyl, an alkyl radical of 4 to 10 carbon atoms, a $C_3$–$C_8$ cycloalkyl group, phenyl and benzyl; said phenyl and benzyl groups being optionally substituted with one or more halogen, $SCH_3$, COOH, $COOCH_3$, $COOCH_2CH_3$, OH, OAc, $OCH_3$, $OCH_2CH_3$, $NO_2$, $NH_2$, $CF_3$ and $C_1$–$C_6$ alkyl;

with the proviso that when m=0, $R_5$ is selected from the group consisting of formyl, $COR_{12}$, $CO_2R_{13}$, and $CR_2(=NOR_4)$, wherein $R_2$ is selected from the group consisting of hydrogen, —OH, a $C_2$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_2$–$C_{10}$ alkyl group, a $C_2$–$C_{10}$ alkenyl group, a $C_2$–$C_{10}$ alkynyl group, phenyl, benzyl and a heteroaromatic radical of the type:

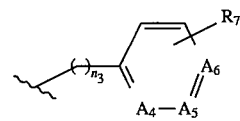

said $C_2$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, —OH, halogen, —$OCH_3$, —SH, —$S(O)n_4CH_3$, and —$NH_2$; and $n_3$=0–2; and $n_4$=0–2.

The novel 1,2-dithiin compounds of formula V are useful as antifungal or anti-infective agents.

The invention still further provides novel 1,2-dithiin derivatives having the formula VI:

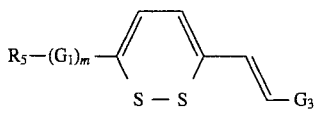

and pharmaceutically acceptable salts thereof, wherein:

$G_1$ is selected from the group consisting of a $C_2$–$C_{10}$ alkyl or branched alkyl group and a $C_3$–$C_{10}$ cycloalkyl group; m=0–1;

$R_5$ is selected from the group consisting of hydrogen, azido, cyano, formyl, halogen, $OR_{10}$, $SR_{11}$, $COR_{12}$, $CR_2(=NOR_4)$ and $CO_2R_{13}$;

$R_{10}$ is selected from the group consisting of hydrogen, a $C_1$–$C_{10}$ alkyl group, a $C_3$–$C_{10}$ cycloalkyl group, an acyl radical of the type

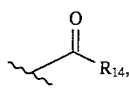

phenyl, benzyl and a 5–6 membered heteroaryl ring; said phenyl, benzyl and 5–6 membered heteroaryl ring being optionally substituted with one or more halogen, $SCH_3$, $COOH$, $COOCH_3$, $OH$, $COOCH_2CH_3$, $OCH_3$, $OCH_2CH_3$, $NO_2$, $CF_3$, $C_1$–$C_6$ alkyl, $NH_2$, and $OAc$;

$R_{14}$ is selected from the group consisting of methyl, ethyl, 1-(methyl)ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and a 5–6 membered ring heteroaryl radical being optionally substituted with one or more $SCH_3$, $COOH$, halogen, $COOCH_3$, $COOCH_2CH_3$, $OH$, $OAc$, $OCH_3$, $OCH_2CH_3$, $NO_2$, $CF_3$, $C_1$–$C_6$ alkyl and $NH_2$;

$R_{11}$ is selected from the group consisting of hydrogen, a $C_1$–$C_{10}$ alkyl group, a $C_3$–$C_{10}$ cycloalkyl group, an acyl radical of the type

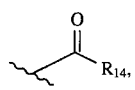

phenyl, benzyl and a 5–6 membered heteroaryl ring; said phenyl, benzyl and 5–6 membered heteroaryl ring being optionally substituted with one or more halogen, $SCH_3$, $COOH$, $COOCH_3$, $COOCH_2CH_3$, $OH$, $OAc$, $OCH_3$, $OCH_2CH_3$, $NO_2$, $CF_3$, $C_1$–$C_6$ alkyl and $NH_2$;

$R_{12}$ is selected from the group consisting of methyl, ethyl, 1-(methyl)ethyl; n-propyl, an alkyl radical of 4 to 10 carbon atoms, a $C_3$–$C_8$ cycloalkyl group, phenyl and benzyl; said phenyl and benzyl groups being optionally substituted with one or more $SCH_3$, $COOH$, $COOCH_3$, $COOCH_2CH_3$, $OH$, $OAc$, $OCH_3$, $OCH_2CH_3$, $NO_2$, $CF_3$, $C_1$–$C_6$ alkyl and $NH_2$, halogen; and $R_{13}$ is selected from the group consisting of hydrogen, methyl, ethyl, 1-(methyl)ethyl, n-propyl, an alkyl radical of 4 to 10 carbon atoms, a $C_3$–$C_8$ cycloalkyl group, phenyl and benzyl; said phenyl and benzyl groups being optionally substituted with one or more halogen, $SCH_3$, $COOH$, $COOCH_3$, $COOCH_2CH_3$, $OH$, $OAc$, $OCH_3$, $OCH_2CH_3$, $NO_2$, $NH_2$, $CF_3$ and $C_1$–$C_6$ alkyl;

with the proviso that when m=0, $R_5$ is selected from the group consisting of cyano, formyl, $COR_{12}$, $CO_2R_{13}$ and $CR_2(=NOR_4)$, $G_3$ is selected from the group consisting of cyano, —CHO, —$COOR_8$ and $CR_1(=NOR_3)$;

$R_8$ is selected from the group consisting of hydrogen, methyl, ethyl, propyl, isopropyl and a C3–C6 alkyl group;

$R_1$ is selected from the group consisting of hydrogen, —OH, a $C_2$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_3$ is selected from the group consisting of hydrogen, a $C_2$–$C_{10}$ alkyl group, a $C_2$–$C_{10}$ alkenyl group, a $C_2$–$C_{10}$ alkynyl group, phenyl, benzyl and a heteroaromatic radical of the type:

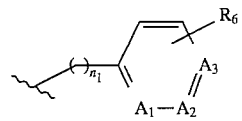

said $C_2$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_1$, $A_2$, and $A_3$ are independently N, or C—H;

$R_6$ is selected from the group consisting of hydrogen, —OH, halogen, —$OCH_3$, —SH, —$S(O)n_2CH_3$, and —$NH_2$;

$n_1$=0–2; and $n_2$=0–2;

with the proviso that when m=0, $R_5$ is selected from the group consisting of cyano, formyl, $COR_{12}$, $CO_2R_{13}$, and $CR_2(=NOR_4)$, wherein $R_2$ is selected from the group consisting of hydrogen, —OH, a $C_2$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_2$–$C_{10}$ alkyl group, a $C_2$–$C_{10}$ alkenyl group, a $C_2$–$C_{10}$ alkynyl group, phenyl, benzyl and a heteroaromatic radical of the type:

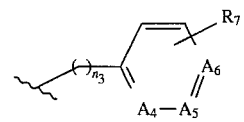

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, —OH, halogen, —$OCH_3$, —SH, —$S(O)n_4CH_3$, and —$NH_2$; and $n_3$=0–2; and $n_4$=0–2.

The novel 1,2-dithiin compounds of formula VI are useful as antifungal or anti-infective agents.

The invention still further provides novel 1,2-dithiin derivatives having the formula VII:

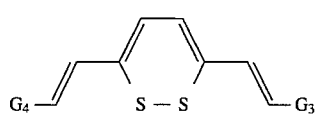

and pharmaceutically acceptable salts thereof, wherein:

$G_3$ is selected from the group consisting of cyano, —CHO, —$COOR_8$ and $CR_1(=NOR_3)$;

$R_8$ is selected from the group consisting of hydrogen, methyl, ethyl, propyl, isopropyl and a C3–C6 alkyl group;

$R_1$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_3$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

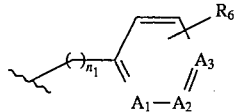

said $C_2$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_1$, $A_2$, and $A_3$ are independently N, or C—H;

$R_6$ is selected from the group consisting of hydrogen, —OH, halogen, —OCH$_3$, —SH, —S(O)n$_2$CH$_3$, and —NH$_2$; and $n_1$=0–2;

$n_2$=0–2;

$G_4$ is selected from the group consisting of cyano, —CHO, —COOR$_9$; and CR$_2$(=NOR$_4$);

$R_9$ is selected from the group consisting of hydrogen, methyl, ethyl, propyl, isopropyl and a C3–C6 alkyl group;

$R_2$ is selected from the group consisting of hydrogen, —OH, a $C_2$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

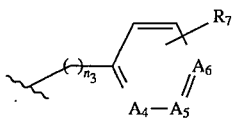

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of C1–C6 alkyl and phenyl;

$A_4$, $A_5$, and $A_6$ are independently N, or C—H;

$R_7$ is selected from the group consisting of hydrogen, —OH, halogen, —OCH$_3$, —SH, —S(O)n$_4$CH$_3$, and —NH$_2$;

$n_3$=0–2; and $n_4$=0–2.

The novel 1,2-dithiin compounds of formula VII are useful as antifungal or anti-infective agents.

In a preferred embodiment, the invention provides novel 1,2-dithiin derivatives having the formula VIII:

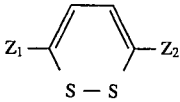

VIII and pharmaceutically acceptable salts thereof, wherein:

$Z_1$ and $Z_2$ are independently selected from the group consisting of —CH$_2$OH, —CHO, —CH=CH—CO$_2$A, —CH=N—OB, —CH=CH—CN, and —CN;

A is selected from the group consisting of a $C_1$–$C_{10}$ alkyl group, a $C_2$–$C_{10}$ alkenyl group and a $C_2$–$C_{10}$ alkynyl group;

B is selected from the group consisting of hydrogen, a $C_2$–$C_{10}$ alkyl group, a $C_2$–$C_{10}$ alkenyl group and a $C_2$–$C_{10}$ alkynyl group; and with the proviso that $Z_1$ and $Z_2$ are not simultaneously —CHO or —CH$_2$OH.

The novel 1,2-dithiin compounds of formula VIII are useful as antifungal or anti-infective agents.

Especially preferred compounds of formula VIII useful as antifungal or anti-infective agents are:

3-(Hydroxymethyl)-6-formyl-1,2-dithiin;

3-(hydroxymethyl)6-[ethyl propenoate-3-yl]-1,2-dithiin;

3-(hydroxymethyl)-6-[methyl propenoate-3-yl]-1,2-dithiin;

3-(hydroxymethyl)-6-[N-methoxyiminomethyl]-1,2-dithiin;

3-(hydroxymethyl)-6-[N-hydroxyiminomethyl]-1,2-dithiin;

3-(hydroxymethyl)-6-[2-cyanoethene-1-yl]-1,2-dithiin;

3-(hydroxymethyl)-6-cyano-1,2-dithiin;

3,6-[bis(N-hydroxyiminomethyl)]-1,2-dithiin; and 3,6-bis(N-methoxyiminomethyl)-1,2-dithiin.

Especially preferred compounds useful as intermediates in the synthesis of the novel 1,2-dithiin compounds of the present invention are:

3-[(tert-Butyldimethylsilyloxy)methyl]-6-formyl-1,2-dithiin;

3-[(tert-Butyldimethylsilyloxy)methyl]-6-[ethyl propenoate-3-yl]-1,2-dithiin;

3-[(tert-Butyldimethylsilyloxy)methyl]-6-[methyl propenoate-3-yl]-1,2-dithiin;

3-[(tert-Butyldimethylsilyloxy)methyl]-6-(N-methoxyiminomethyl)-1,2-dithiin;

3-[(tert-Butyldimethylsilyloxy)methyl]-6-(N-hydroxyiminomethyl)-1,2-dithiin;

3-[(tert-Butyldimethylsilyloxy)methyl]-6-[2-cyanoethene-1-yl]-1,2-dithiin; and

3-[(tert-Butyldimethylsilyloxy)methyl]-6-cyano-1,2-dithiin.

The present invention may be understood more fully by reference to the following figures, detailed description and illustrative examples which are intended to exemplify non-limiting embodiments of the invention.

4. DESCRIPTION OF THE FIGURES

FIG. 1 is a flow chart describing methods for synthesizing the compounds of the present invention.

5. DETAILED DESCRIPTION OF THE INVENTION 5.1 SYNTHESIS OF THE 1,2-DITHIIN COMPOUNDS

The 1,2-dithiin derivatives of the present invention can be prepared by synthetic methods outlined below. The dithiin precursors 3-[(tert-butyldimethylsilyloxy)methyl]-3-(hydroxymethyl)-1,2-dithiin and 3,6-[bis(hydroxymethyl)]-1,2-dithiin are prepared as previously described in U.S. patent application Ser. No. 08/212,096, herein incorporated by reference, and in M. Koreeda and W. Yang, Synlett, 1994, 201.

As shown in FIG. 1, the compounds of formulas IV, V and VI can be obtained from the compounds of formula III and the compounds of formulas II and VII can be obtained from the compounds of formula I.

For example, a mono-protected 3,6-bis(hydroxymethyl)-1,2-dithiin, such as 3-[tert-butyldimethylsilyloxy)methyl]-6-(hydroxymethyl)-1,2-dithiin, is oxidized to an aldehyde with the Dess-Martin periodinane reagent, via Swern oxidation conditions, with Collins Reagent or by any other methods known by those of skill in the art to form aldehydes from primary alcohols, to yield a compound of formula III. The compound of formula III is then reacted with hydroxylamine to yield the corresponding oxime which is then dehydrated and subsequently deprotected to yield compounds of formula V. If the tert-butyldimethylsilyloxy protecting group is used, it is preferably removed in the presence of acid such as acetic acid and in the presence of a fluoride source, such as tetrabutylammonium fluoride.

Likewise, monoprotected compounds of formula III, such as 3-[tert-butyldimethylsilyloxy)methyl]-6-(hydroxymethyl)-1,2-dithiin, are condensed with an alkoxylamine, such as methoxylamine, to yield after deprotection as stated above, compounds of formula IV. Preferably, the alkoxylamine is used as its acid salt, most preferably its hydrochloric acid salt.

Compounds of formula III, wherein $R_1$ is hydrogen, can be converted to compounds of formula VI. For example, treatment of the silyloxy-functionalized aldehyde described above with a reagent having active hydrogens and capable of undergoing a Claisen-Schmidt-type or Horner-Emmons-Wittig-type condensation therewith, such as an alkyl acetate, a trialkylphosphonoacetate, or a dialkylcyanomethylphosphonate in the presence of a strong base such as butyllithium or sodium amide, followed by deprotection as described above, yields compounds of formula VI.

Similarly, compounds of formula I, such as 3,6-bis-(formyl)-1,2-dithiin, obtained from the Dess-Martin, Swern or Collins oxidation of 3,6-bis(hydroxymethyl)-1,2-dithiin (U.S. Ser. No. 08/212,096 encorporated herein by reference and M. Koreeda et al., Synlett, 1994, 201) can be treated sequentially with a variety of alkoxylamines, such as for example propoxyl, ethoxyl and preferably methoxylamine, to yield O-alkyloximes of formula II. Preferably, the alkoxylamine is used as its acid salt, most preferably its hydrochloric acid salt.

In addition, compounds of formula I, specifically 3,6-bis(formyl)-1,2-dithiin, can be treated with reagents having active hydrogens and capable of undergoing a Claisen-Schmidt-type or Horner-Emmons-Wittig type condensation therewith, as described above for compounds of formula III, to obtain compounds of formula VII.

The compounds of formula VIII can be obtained by using a combination of methods described above for the compounds of formulas II and IV–VII.

5.2 METHODS FOR USE OF 1,2-DITHIIN COMPOUNDS

Due to the potent activities of the presently described 1,2-dithiin compounds, the 1,2-dithiin compounds of the present invention are useful as antifungal or anti-infective agents in veterinary and human medicine against a wide range of pathogens. Fungal species which are inhibited by the 1,2-dithiin compounds of the present invention include, but are not limited to, *Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immitis,* and *Histoplasma capsulatum*. Viruses which are inhibited by the 1,2-dithiin compounds of the present invention include *Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdlovirus, Togavirus,* and *Hepadnavirus*. Bacteria which are inhibited by the 1,2-dithiin compounds include *Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis, Streptococcus pyogenes; Straptococcus pneumonia, Viridans streptococci, Haemophilus influenzae, Proteus mirabilis, proteus vulgaris* and *Bacterioides fragilis.*

Additionally, the 1,2-dithiin compounds of the present invention are useful as an active agent in an antiseptic, disinfectant or cleaning composition which has fungicidal and/or fungistatic, and/or anti-bacterial and/or anti-viral properties. According to this embodiment of the invention, the novel 1,2-dithiins are used to retard or inhibit fungal and/or bacterial growth on surfaces of a variety of materials including, but not limited to animal, including human, skin, and surfaces of inanimate objects used, for example, in homes or offices. The compounds may be used in such compositions either as the sole active agent or in combination with other active anti-fungal and/or anti-bacterial agents. In a specific illustrative example (see Section 6, infra), the compounds are used to inhibit fungal growth, for example, on laboratory glassware or on bathroom surfaces.

When administered to a mammal for veterinary use or to a human for clinical use, the 1,2-dithiin compounds can be used alone or may be combined with any physiologically acceptable carrier such as water, an aqueous solution, normal saline, or any other physiologically accetable excipient. In general, the dosage would range from about 0.1–500 mg/kg mg/kg/day, preferably about 1–100 mg/kg/day.

The 1,2-dithiin compounds can be administered by a number of routes including, but not limited to: orally; topically; nasally; parenterally; by aerosol; by injection including, but not limited to intraperitoneally, subcutaneously, intramuscularly, etc.; and combinations thereof. The preferred route of administration is oral.

According to an embodiment of the invention, pharmaceutical compositions comprising the novel 1,2-dithiin compounds having the structure of formula I $$\underset{O}{\overset{R_2}{\diagdown}}\!\!\!\diagup\!\!\!\overset{}{\diagdown}\!\!\!\diagup\!\!\!\underset{O}{\overset{R_1}{\diagdown}} \quad \text{I}$$
$$\phantom{xxxxxx} S-S$$

and pharmaceutically acceptable salts thereof, wherein:

$R_1$ is selected from the group consisting of hydrogen, —OH, a $C_2$–$C_{10}$ alkyl group, a $C_2$–$C_{10}$ alkenyl group and a $C_1$–$C_{10}$ alkynyl group; said alkyl, alkenyl or alkynyl groups being optionally substituted with one or more groups selected from the group consisting of $C_1$–$C_6$ alkyl and phenyl; and $R_2$ is selected from the group consisting of hydrogen, —OH, a $C_2$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl, with the proviso that $R_1$ and $R_2$ are not simultaneously hydrogen, are advantageously useful in veterinary and human medicine as antifungal or anti-infective agents.

According to a further embodiment of the invention, pharmaceutical compositions comprising the novel 1,2-dithiin compounds having the structure of formula II:

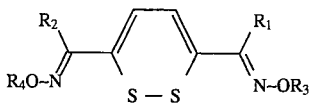

and pharmaceutically acceptable salts thereof, wherein:

$R_1$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_2$ is selected from the group consisting of hydrogen, —OH, a $C_2$–$C_{10}$ alkyl group, a $C_2$–$C_{10}$ alkenyl group and a $C_1$–$C_{10}$ alkynyl group; said alkyl, alkenyl or alkynyl groups being optionally substituted with one or more groups selected from the group consisting of $C_1$–$C_6$ alkyl and phenyl;

$R_3$ is selected from the group consisting of hydrogen, a $C_2$–$C_{10}$ alkyl group, a $C_2$–$C_{10}$ alkenyl group, a $C_2$–$C_{10}$ alkynyl group, phenyl, benzyl and a heteroaromatic radical of the type:

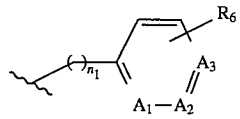

said $C_2$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_1$, $A_2$, and $A_3$ are independently N, or C—H;

$R_6$ is selected from the group consisting of hydrogen, —OH, halogen, —OCH$_3$, —SH, —S(O)n$_2$CH$_3$, and —NH$_2$;

$n_1$=0–2;

$n_2$=0–2;

$R_4$ is selected from the group consisting of hydrogen, a $C_2$–$C_{10}$ alkyl group, a $C_2$–$C_{10}$ alkenyl group, a $C_2$–$C_{10}$ alkynyl group, phenyl, benzyl and a heteroaromatic radical of the type:

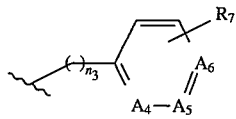

said $C_2$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, —OH, halogen, —OCH$_3$, —SH, —S(O)n$_4$CH$_3$, and —NH$_2$;

$n_3$=0–2

$n_4$=0–2; and with the proviso that $R_1$ and $R_2$ are not simultaneously —OH, are advantageously useful in veterinary and human medicine as antifungal or anti-infective agents.

In a still further embodiment of the invention, pharmaceutical compositions comprising the novel 1,2-dithiin compounds having the formula III:

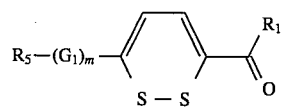

and pharmaceutically acceptable salts thereof, wherein:

$R_1$ is selected from the group consisting of hydrogen, —OH, a $C_2$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$G_1$ is selected from the group consisting of a $C_2$–$C_{10}$ alkyl or branched alkyl group and a $C_3$–$C_{10}$ cycloalkyl group;

m=0–1;

$R_5$ is selected from the group consisting of hydrogen, azido, cyano, formyl, halogen, OR$_{10}$, SR$_{11}$, COR$_{12}$, CR$_2$(=NOR$_4$) and CO$_2$R$_{13}$;

$R_{10}$ is selected from the group consisting of hydrogen, a $C_2$–$C_{10}$ alkyl group, a $C_3$–$C_{10}$ cycloalkyl group, an acyl radical of the type

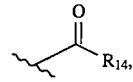

phenyl, benzyl and a 5–6 membered heteroaryl ring; said phenyl, benzyl and 5–6 membered heteroaryl ring being optionally substituted with one or more halogen, SCH$_3$, COOH, COOCH$_3$, OH, COOCH$_2$CH$_3$, OCH$_3$, OCH$_2$CH$_3$, NO$_2$, CF$_3$, $C_1$–$C_6$ alkyl, NH$_2$, and OAc;

$R_{14}$ is selected from the group consisting of methyl, ethyl, 1-(methyl)ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and a 5–6 membered ring heteroaryl radical being optionally substituted with one or more halogen, SCH$_3$, COOH, COOCH$_3$, COOCH$_2$CH$_3$, OH, OAc, OCH$_3$, OCH$_2$CH$_3$, NO$_2$, CF$_3$, $C_1$–$C_6$ alkyl and NH$_2$;

$R_{11}$ is selected from the group consisting of hydrogen, a $C_1$–$C_{10}$ alkyl group, a $C_3$–$C_{10}$ cycloalkyl group, an acyl radical of the type

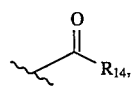

phenyl, benzyl and a 5–6 membered heteroaryl ring; said phenyl, benzyl and 5–6 membered heteroaryl ring being optionally substituted with one or more halogen, SCH$_3$, COOH, COOCH$_3$, COOCH$_2$CH$_3$, OH, OAc, OCH$_3$, OCH$_2$CH$_3$, NO$_2$, CF$_3$, $C_1$–$C_6$ alkyl and NH$_2$;

$R_{12}$ is selected from the group consisting of methyl, ethyl, 1-(methyl)ethyl; n-propyl, an alkyl radical of 4 to 10 carbon atoms, a $C_3$–$C_8$ cycloalkyl group, phenyl and benzyl; said phenyl and benzyl groups being optionally substituted with one or more halogen, SCH$_3$, COOH, COOCH$_3$, COOCH$_2$CH$_3$, OH, OAc, OCH$_3$, OCH$_2$CH$_3$, NO$_2$, CF$_3$, $C_1$–$C_6$ alkyl and NH$_2$; and $R_{13}$ is selected from the group consisting of hydrogen, methyl, ethyl, 1-(methyl)ethyl, n-propyl, an alkyl radical of 4 to 10 carbon atoms, a $C_3$–$C_8$ cycloalkyl group, phenyl and benzyl; said phenyl and benzyl groups being optionally substituted with one or more SCH$_3$, COOH, COOCH$_3$, COOCH$_2$CH$_3$, OH, OAc, OCH$_3$, OCH$_2$CH$_3$, NO$_2$, CF$_3$, $C_1$–$C_6$ alkyl, NH$_2$ and halogen;

with the proviso that when m=0, $R_5$ is selected from the group consisting of cyano, formyl, COR$_{12}$, CO$_2$R$_{13}$, and $CR_2(=NOR_4)$, except that when $R_1$ is hydrogen and m=0, $R_5$ is not formyl;

wherein $R_2$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

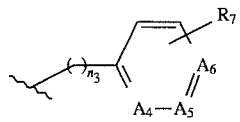

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, —OH, halogen, —OCH$_3$, —SH, —S(O)n$_4$CH$_3$, and —NH$_2$;
$n_3$=0–2; and
$n_4$=0–2, are advantageously useful in veterinary and human medicine as antifungal or anti-infective agents.

In a still further embodiment of the invention, pharmaceutical compositions comprising the novel 1,2-dithiin compounds having the structure of formula IV:

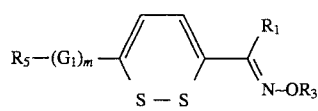

and pharmaceutically acceptable salts thereof, wherein:

$R_1$ is selected from the group consisting of hydrogen, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_3$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

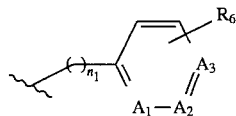

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_1$, $A_2$, and $A_3$ are independently N, or C—H;

$R_6$ is selected from the group consisting of hydrogen, —OH, halogen, —OCH$_3$, —SH, —S(O)n$_2$CH$_3$, and —NH$_2$;
$n_1$=0–2;
$n_2$=0–2;

$G_1$ is selected from the group consisting of a $C_1$–$C_{10}$ alkyl or branched alkyl group and a $C_3$–$C_{10}$ cycloalkyl group;
m=0–1;

$R_5$ is selected from the group consisting of hydrogen, azido, cyano, formyl, halogen, $OR_{10}$, $SR_{11}$, $COR_{12}$, $CR_2(=NOR_4)$ and $CO_2R_{13}$;

$R_{10}$ is selected from the group consisting of hydrogen, a $C_1$–$C_{10}$ alkyl group, a $C_3$–$C_{10}$ cycloalkyl group, an acyl radical of the type

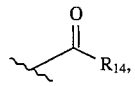

phenyl, benzyl and a 5–6 membered heteroaryl ring; said phenyl, benzyl and 5–6 membered heteroaryl ring being optionally substituted with one or more halogen, SCH$_3$, COOH, COOCH$_3$, OH, COOCH$_2$CH$_3$, OCH$_3$, OCH$_2$CH$_3$, NO$_2$, CF$_3$, $C_1$–$C_6$ alkyl, NH$_2$, and OAc;

$R_{14}$ is selected from the group consisting of methyl, ethyl, 1-(methyl)ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and a 5–6 membered ring heteroaryl radical being optionally substituted with one or more SCH$_3$, COOH, halogen, COOCH$_3$, COOCH$_2$CH$_3$, OH, OAc, OCH$_3$, OCH$_2$CH$_3$, NO$_2$, CF$_3$, $C_1$–$C_6$ alkyl and NH$_2$;

$R_{11}$ is selected from the group consisting of hydrogen, a $C_1$–$C_{10}$ alkyl group, a $C_3$–$C_{10}$ cycloalkyl group, an acyl radical of the type

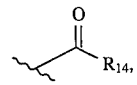

phenyl, benzyl and a 5–6 membered heteroaryl ring; said phenyl, benzyl and 5–6 membered heteroaryl ring being optionally substituted with one or more halogen, SCH$_3$, COOH, COOCH$_3$, COOCH$_2$CH$_3$, OH, OAc, OCH$_3$, OCH$_2$CH$_3$, NO$_2$, CF$_3$, $C_1$–$C_6$ alkyl and NH$_2$;

$R_{12}$ is selected from the group consisting of methyl, ethyl, 1-(methyl)ethyl; n-propyl, an alkyl radical of 4 to 10 carbon atoms, a $C_3$–$C_8$ cycloalkyl group, phenyl and benzyl; said phenyl and benzyl groups being optionally substituted with one or more SCH$_3$, COOH, COOCH$_3$, COOCH$_2$CH$_3$, OH, OAc, OCH$_3$, OCH$_2$CH$_3$, NO$_2$, CF$_3$, $C_1$–$C_6$ alkyl, NH$_2$, and halogen;

$R_{13}$ is selected from the group consisting of hydrogen, methyl, ethyl, 1-(methyl)ethyl, n-propyl, an alkyl radical of 4 to 10 carbon atoms, a $C_3$–$C_8$ cycloalkyl group, phenyl and benzyl; said phenyl and benzyl groups being optionally substituted with one or more halogen, SCH$_3$, COOH, COOCH$_3$, COOCH$_2$CH$_3$, OH, OAc, OCH$_3$, OCH$_2$CH$_3$, NO$_2$, NH$_2$, CF$_3$ and $C_1$–$C_6$ alkyl;

with the proviso that when m=0, $R_5$ is selected from the group consisting of cyano, formyl, $COR_{12}$, $CO_2R_{13}$, and $CR_2(=NOR_4)$, wherein $R_2$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

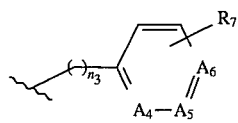

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, halogen, —OH, —OCH$_3$, —SH, —S(O)n$_4$CH$_3$, and —NH$_2$; and $n_3$=0–2; and
$n_4$=0–2, are advantageously useful in veterinary and human medicine as antifungal or anti-infective agents.

In a still further embodiment of the invention, pharmaceutical compositions comprising the novel 1,2-dithiin compounds having the structure of formula V:

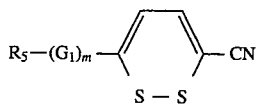

and pharmaceutically acceptable salts thereof, wherein:

$G_1$ is selected from the group consisting of a $C_1$–$C_{10}$ alkyl or branched alkyl group and a $C_3$–$C_{10}$ cycloalkyl group; m=0–1;

$R_5$ is selected from the group consisting of hydrogen, azido, cyano, formyl, halogen, $OR_{10}$, $SR_{11}$, $COR_{12}$, $CR_2(=NOR_4)$ and $CO_2R_{13}$;

$R_{10}$ is selected from the group consisting of hydrogen, a $C_2$–$C_{10}$ alkyl group, a $C_3$–$C_{10}$ cycloalkyl group, an acyl radical of the type

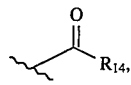

phenyl, benzyl and a 5–6 membered heteroaryl ring; said phenyl, benzyl and 5–6 membered heteroaryl ring being optionally substituted with one or more halogen, SCH$_3$, COOH, COOCH$_3$, OH, COOCH$_2$CH$_3$, OCH$_3$, OCH$_2$CH$_3$, NO$_2$, CF$_3$, $C_1$–$C_6$ alkyl, NH$_2$, and OAc;

$R_{14}$ is selected from the group consisting of methyl, ethyl, 1-(methyl)ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and a 5–6 membered ring heteroaryl radical being optionally substituted with one or more SCH$_3$, COOH, halogen, COOCH$_3$, COOCH$_2$CH$_3$, OH, OAc, OCH$_3$, OCH$_2$CH$_3$, NO$_2$, CF$_3$, $C_1$–$C_6$ alkyl and NH$_2$;

$R_{11}$ is selected from the group consisting of hydrogen, a $C_1$–$C_{10}$ alkyl group, a $C_3$–$C_{10}$ cycloalkyl group, an acyl radical of the type

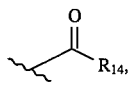

phenyl, benzyl and a 5–6 membered heteroaryl ring; said phenyl, benzyl and 5–6 membered heteroaryl ring being optionally substituted with one or more halogen, SCH$_3$, COOH, COOCH$_3$, COOCH$_2$CH$_3$, OH, OAc, OCH$_3$, OCH$_2$CH$_3$, NO$_2$, CF$_3$, $C_1$–$C_6$ alkyl and NH$_2$;

$R_{12}$ is selected from the group consisting of methyl, ethyl, 1-(methyl)ethyl; n-propyl, an alkyl radical of 4 to 10 carbon atoms, a $C_3$–$C_8$ cycloalkyl group, phenyl and benzyl; said phenyl and benzyl groups being optionally substituted with one or more SCH$_3$, COOH, COOCH$_3$, COOCH$_2$CH$_3$, OH, OAc, OCH$_3$, OCH$_2$CH$_3$, NO$_2$, CF$_3$, $C_1$–$C_6$ alkyl and NH$_2$, halogen; and $R_{13}$ is selected from the group consisting of hydrogen, methyl, ethyl, 1-(methyl)ethyl, n-propyl, an alkyl radical of 4 to 10 carbon atoms, a $C_3$–$C_8$ cycloalkyl group, phenyl and benzyl; said phenyl and benzyl groups being optionally substituted with one or more halogen, SCH$_3$, COOH, COOCH$_3$, COOCH$_2$CH$_3$, OH, OAc, OCH$_3$, OCH$_2$CH$_3$, NO$_2$, NH$_2$, CF$_3$ and $C_1$–$C_6$ alkyl;

with the proviso that when m=0, $R_5$ is selected from the group consisting of formyl, $COR_{12}$, $CO_2R_{13}$, and $CR_2(=NOR_4)$, wherein $R_2$ is selected from the group consisting of hydrogen, —OH, a $C_1$–$C_{10}$ alkyl group, a $C_2$–$C_{10}$ alkenyl group and a $C_1$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

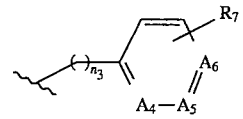

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, —OH, halogen, —OCH$_3$, —SH, —S(O)n$_4$CH$_3$, and —NH$_2$; and $n_3$=0–2; and
$n_4$=0–2, are advantageously useful in veterinary and human medicine as antifungal or anti-infective agents.

In a still further embodiment of the invention, pharmaceutical compositions comprising the novel 1,2-dithiin compounds having the structure of formula VI:

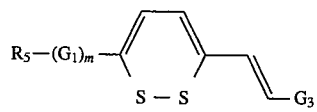

and pharmaceutically acceptable salts thereof, wherein:

$G_1$ is selected from the group consisting of a $C_1$–$C_{10}$ alkyl or branched alkyl group and a $C_3$–$C_{10}$ cycloalkyl group; m=0–1;

$R_5$ is selected from the group consisting of hydrogen, azido, cyano, formyl, halogen, $OR_{10}$, $SR_{11}$, $COR_{12}$, $CR_2(=NOR_4)$ and $CO_2R_{13}$;

$R_{10}$ is selected from the group consisting of hydrogen, a $C_1$–$C_{10}$ alkyl group, a $C_3$–$C_{10}$ cycloalkyl group, an acyl radical of the type

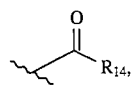

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, OH, $COOCH_2CH_3$, $OCH_3$, $OCH_2CH_3$, $NO_2$, $CF_3$, $C_1$–$C_6$ alkyl, $NH_2$, and OAc;

$R_{14}$ is selected from the group consisting of methyl, ethyl, 1-(methyl)ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and a 5–6 membered ring heteroaryl radical being optionally substituted with one or more $SCH_3$, COOH, halogen, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{11}$ is selected from the group consisting of hydrogen, a $C_1$–$C_{10}$ alkyl group, a $C_3$–$C_{10}$ cycloalkyl group, an acyl radical of the type

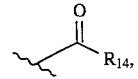

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{12}$ is selected from the group consisting of methyl, ethyl, 1-(methyl)ethyl; n-propyl, an alkyl radical of 4 to 10 carbon atoms, a $C_3$–$C_8$ cycloalkyl group, phenyl and benzyl; said phenyl and benzyl groups being optionally substituted with one or more $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$, halogen; and $R_{13}$ is selected from the group consisting of hydrogen, methyl, ethyl, 1-(methyl)ethyl, n-propyl, an alkyl radical of 4 to 10 carbon atoms, a $C_3$–$C_8$ cycloalkyl group, phenyl and benzyl; said phenyl and benzyl groups being optionally substituted with one or more halogen, $SCH_3$, COOH, $COOCH_3$, $COOCH_2CH_3$, OH, OAc, $OCH_3$, $OCH_2CH_3$, $NO_2$, $NH_2$, $CF_3$ and $C_1$–$C_6$ alkyl;

with the proviso that when m=0, $R_5$ is selected from the group consisting of cyano, formyl, $COR_{12}$, $CO_2R_{13}$ and $CR_2(=NOR_4)$, $G_3$ is selected from the group consisting of cyano, —CHO, —$COOR_8$ and $CR_1(=NOR_3)$;

$R_8$ is selected from the group consisting of hydrogen, methyl, ethyl, propyl, isopropyl and a C3–C6 alkyl group;

$R_1$ is selected from the group consisting of hydrogen, —OH, a $C_1$–$C_{10}$ alkyl group, a $C_2$–$C_{10}$ alkenyl group and a $C_1$–$C_{10}$ alkynyl group; said alkyl, alkenyl or alkynyl groups being optionally substituted with one or more groups selected from the group consisting of $C_1$–$C_6$ alkyl and phenyl;

$R_3$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

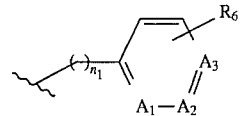

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_1$, $A_2$, and $A_3$ are independently N, or C—H;

$R_6$ is selected from the group consisting of hydrogen, —OH, halogen, —$OCH_3$, —SH, —$S(O)n_2CH_3$, and —$NH_2$;

$n_1$=0–2; and $n_2$=0–2;

with the proviso that when m=0, $R_5$ is selected from the group consisting of cyano, formyl, $COR_{12}$, $CO_2R_{13}$, and $CR_2(=NOR_4)$, wherein $R_2$ is selected from the group consisting of hydrogen, —OH, a $C_2$–$C_{10}$ alkyl group, a $C_2$–$C_{10}$ alkenyl group and a $C_1$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

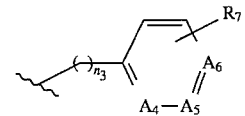

said $C_2$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, —OH, halogen, —$OCH_3$, —SH, —$S(O)n_4CH_3$, and —$NH_2$; and $n_3$=0–2; and $n_4$=0–2, are advantageously useful in veterinary and human medicine as antifungal or anti-infective agents.

In a still further embodiment of the invention, pharmaceutical compositions comprising the novel 1,2-dithiin compounds having the structure of formula VII:

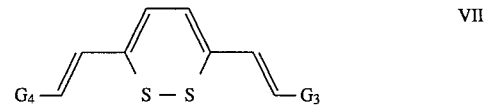

and pharmaceutically acceptable salts thereof, wherein:

$G_3$ is selected from the group consisting of cyano, —CHO, —$COOR_8$ and $CR_1(=NOR_3)$;

$R_8$ is selected from the group consisting of hydrogen, methyl, ethyl, propyl, isopropyl and a C3–C6 alkyl group;

$R_1$ is selected from the group consisting of hydrogen, —OH, a $C_1$–$C_{10}$ alkyl group, a $C_2$–$C_{10}$ alkenyl group and a $C_1$–$C_{10}$ alkynyl group; said alkyl, alkenyl or alkynyl groups being optionally substituted with one or more groups selected from the group consisting of $C_1$–$C_6$ alkyl and phenyl;

$R_3$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

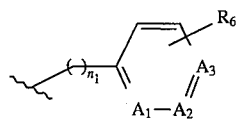

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_1$, $A_2$, and $A_3$ are independently N, or C—H;

$R_6$ is selected from the group consisting of hydrogen, —OH, halogen, —OCH$_3$, —SH, —S(O)n$_2$CH$_3$, and —NH$_2$; and $n_1$=0–2;

$n_2$=0–2;

$G_4$ is selected from the group consisting of cyano, —CHO, —COOR$_9$; and CR$_2$(=NOR$_4$);

$R_9$ is selected from the group consisting of hydrogen, methyl, ethyl, propyl, isopropyl and a C3–C6 alkyl group;

$R_2$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

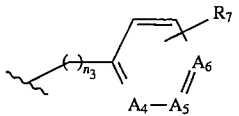

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, —OH, halogen, —OCH$_3$, —SH, —S(O)n$_4$CH$_3$, and —NH$_2$;

$n_3$=0–2; and $n_4$=0–2, are advantageously useful in veterinary and human medicine as antifungal or anti-infective agents.

In a preferred embodiment, pharmaceutical compositions comprising the novel 1,2-dithiin compounds having the structure of formula VIII:

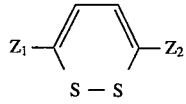

VIII and pharmaceutically acceptable salts thereof, wherein:

$Z_1$ and $Z_2$ are independently selected from the group consisting of —CH$_2$OH, —CHO, —CH=CH—CO$_2$A, —CH=N—OB, —CH=CH—CN, and —CN;

A is selected from the group consisting of a $C_1$–$C_{10}$ alkyl group, a $C_2$–$C_{10}$ alkenyl group and a $C_2$–$C_{10}$ alkynyl group;

B is selected from the group consisting of hydrogen, a $C_1$–$C_{10}$ alkyl group, a $C_2$–$C_{10}$ alkenyl group and a $C_2$–$C_{10}$ alkynyl group; and with the proviso that $Z_1$ and $Z_2$ are not simultaneously —CHO or —CH$_2$OH;

useful as antifungal or anti-infective agents.

A preferred mode of this embodiment of the invention encompasses pharmaceutical compositions comprising compounds selected from the group consisting of:

3-(Hydroxymethyl)-6-formyl-1,2-dithiin;

3-(hydroxymethyl)6-[ethyl propenoate-3-yl]-1,2-dithiin;

3-(hydroxymethyl)-6-[methyl propenoate-3-yl]-1,2-dithiin;

3-(hydroxymethyl)-6-[N-methoxyiminomethyl]-1,2-dithiin;

3-(hydroxymethyl)-6-[N-hydroxyiminomethyl]-1,2-dithiin;

3-(hydroxymethyl)-6-[2-cyanoethene-1-yl]-1,2-dithiin;

3-(hydroxymethyl)-6-cyano-1,2-dithiin;

3,6-bis(N-hydroxyiminomethyl)]-1,2-dithiin;

3,6-bis[N-methoxyiminomethyl)]-1,2-dithiin; and pharmaceutically acceptable salts thereof; as antifungal or anti-infective agents.

By "pharmaceutically acceptable" is meant compatible with other ingredients used in combination with the 1,2-dithiin compounds or compositions of the present invention and non-deleterious to the recipient.

Such pharmaceutically acceptable salts include, but are not limited to hydrochloride, hydrobromide, hydroiodide, phosphate, sulfate, acetate, succinate, ascorbate, tatrate, gluconate, benzoate, malate, fumarate, citrate, sodium, ammonium and potassium. In general, the compositions are prepared by uniformly and intimately bringing into association the active ingredient(s) with a liquid carrier or finely divided solid carrier or both, and then if necessary shaping the product. By "active ingredient(s)" is meant one or more of the 1,2-dithiin compounds of the present invention.

Compositions of the present invention suitable for oral administration may be administered as discrete units such as capsules, cachers or tablets each containing a predetermined amount of the active ingredient(s); as a powder or granules; as a solution or a suspension in an aqueous liquid or a non-aqueous liquid; or as an oil-in-water liquid emulsion or a water-in-oil liquid emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent known to those skilled in the art. Molded tablets may be made by molding in a suitable machine a mixture of the powdered compound moistened with an inert liquid diluent. The tablets may optionally be coated or scored and may be formulated so as to provide slow or controlled release of the active ingredient(s) therein.

Formulations suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Compositions suitable for topical administration to the skin may be administered as ointments, creams, gels, and pastes comprising the active ingredient(s) to be administered in a pharmaceutically acceptable carrier. A preferred topical delivery system is a transdermal patch containing the ingredient to be administered.

Compostions suitable for nasal administration wherein the carrier is a solid, include a coarse powder having a particle size, for example, in the range 20 to 500 microns which is administered in the manner in which snuff is taken, i.e. by rapid inhalation through the nasal passage from a container of the powder held close up to the nose. Suitable formulations for nasal administration wherein the carrier is a liquid, as for example a nasal spray or as nasal drops, include aqueous or oily solutions of the active ingredient(s).

Compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose containers, for example, sealed ampules and vials, and may be stored in a freeze-dried (lyophilized) condition requiring only the addition of a sterile liquid carrier, for example water for injections, immediately prior to use. Extemporous injection solutions and suspensions may be prepared from sterile powders, granules, and tablets of the kind described above.

Preferred unit dosage formulations are those containing a daily dose or unit, daily sub-dose, as recited above, or an appropriate fraction thereof, of the administered active ingredient(s).

It should be understood that in addition to the additives particularly mentioned above the compositions of this invention may include other agents conventional in the art having regard to the type of composition in question, for example, those suitable for oral administration may include flavoring agents.

The 1,2-dithiin compounds described herein intended to be used as antifungal agents can be administered intravenously in a range of about 0.1 to about 400 mg/kg body weight, preferably about 0.1 to about 25 mg/kg body weight.

The 1,2-dithiin compounds described herein intended to be used as antifungal agents can be administered intraperitoneally in a range of about 0.1 to about 400 mg/kg body weight, preferably about 0.1 to about 25 mg/kg body weight.

The 1,2-dithiin compounds described herein intended to be used as antifungal agents can be administered subcutaneously in a range of about 1 to about 400 mg/kg body weight, preferably about 1.0 to about 40 mg/kg body weight.

The 1,2-dithiin compounds described herein intended to be used as antifungal agents can be administered intramuscularly in a range of about 1 to about 400. mg/kg body weight, preferably about 1.0 to about 40 mg/kg body weight.

The 1,2-dithiin compounds described herein intended to be used as antifungal agents can be administered orally in a range of about 1 to about 400 mg/kg body weight, preferably about 1.0 to about 50 mg/kg body weight.

The 1,2-dithiin compounds described herein intended to be used as antifungal agents can be administered topically including to skin, ocular, and oral tissues in a range of about 1.0 to about 15% by weight of the formulation, preferably about 5.0 to about 15% by weight of the formulation.

The 1,2-dithiin compounds described herein intended to be used as antifungal agents can be administered by aerosol in a range of about 1.0 to about 400 mg/kg body weight, preferably about 5.0 to about 50 mg/kg body weight/day.

The novel 1,2-dithiin compounds described herein are also useful as an active agent in an antiseptic, disinfectant or cleaning composition which has fungicidal and/or fungistatic, and/or anti-bacterial and/or anti-viral properties. In one illustrative example, the antiseptic, disinfectant or cleaning composition can be used to disinfect or clean laboratory glassware such as petri dishes, agar plates, etc. or containers use to contain media for growing or maintaining fungal, bacterial or viral cultures. Such antiseptic, disinfectant or cleaning compositions embraced by the present invention can be used to clean glassware or containers as described above which have been used at least once for growing or maintaining fungal, bacterial or viral cultures. Alternatively, the antiseptic, disinfectant or cleaning composition can be used to disinfect or clean glassware or containers which have not yet been used. In another illustrative example, the antiseptic, disinfectant or cleaning composition can be used to disinfect or clean surfaces or areas of a home, such as sinks, tubs, bathroom floors, etc., which have been used by a person infected with a fungal, bacterial or viral infection.

The following series of Examples are presented by way of illustration and not by way of limitation on the scope of the invention.

6. EXAMPLE: SYNTHESIS OF 1–2 DITHIIN COMPOUNDS 6.1 MATERIALS AND METHODS

Tetrahydrofuran (THF) was distilled from potassium/benzophenone; benzene, triethylamine and methylene chloride were distilled from calcium hydride. Anhydrous dimethylformamide (DMF), anhydrous dimethoxyethane (glyme) and anhydrous pyridine were obtained from Aldrich. All reactions involving dithiins were done under red light (darkroom!) conditions only. All moisture-sensitive reactions were done under a nitrogen atmosphere, using dry solvents, and all reactions were monitored by TLC. Reaction mixtures following workup were dried over $Na_2SO_4$ or $MgSO_4$ and then filtered before rotary evaporation. Evaporation of solvents was done at room temperature unless otherwise noted. The Dess-Martin periodinane reagent was prepared according to the recent procedure reported by Ireland [Ireland, R. E.; Liu, L. *J. Org. Chem.* 1993, 58, 2899]. Bis[4-(2,2-dimethyl-1,3-dioxolyl)methyl]carbodiimide (BDDC) was prepared by the procedure of Rapoport [Gibson, F. S.; Park, M. S.; Rapoport, H. *J. Org. Chem.* 1994, 59, 7503]. All other reagents were used as received. Flash column chromatography was performed on E. Merck 60 silica gel (230–400 mesh) using nitrogen pressure. TLC was performed on E. Merck Kieselgel 60 $F_{254}$ aluminum plates, and the developed plates were visualized by UV or visible light. $^1H$ and $^{13}C$ NMR were recorded on a Varian Unity Plus 400 MHz or a Varian Unity 400 MHz spectrometer with chloroform as an internal reference unless otherwise noted. NMR shifts were expressed in ppm downfield from internal tetramethylsilane, and NMR coupling constants are reported in Hertz. NMR assignments were determined on the basis of COSY, NOESY, HMQC, HMBC and DEPT experiments performed on selected intermediates. Low resolution mass spectra were recorded on a Kratos MS50 or a Kratos Profile spectrometer. High resolution mass spectra were recorded at Shaman Pharmaceuticals on a Kratos MS50 spectrometer, or were performed by the Analytical Services Department at the University of California, Berkeley. Elemental analyses were performed by the Analytical Services Department at the University of California, Berkeley. Analytical samples of most 1,2-dithiins were purified by reverse-phase HPLC. Preparative HPLC was performed using a Rainin HPLC equipped with two SD-1 pumps and UV-1 detector, with detection at 254 nm, and using a Hamilton PRP-1 reverse-phase column with an acetonitrile-water solvent gradient. Analytical HPLC was performed on a Rainin HPLC equipped with two SD-1 pumps, a PDA-1 diode array detector, and a Sedex 55 light scattering detector, using a Hamilton PRP-1 reverse-phase column with an acetonitrile-water solvent gradient. Melting points were determined using a Buchi model 535 melting point apparatus and are uncorrected.

6.2 1,2-DITHIIN COMPOUNDS SYNTHESIZED

Example 1

3-[(tert-Butyldimethylsilyloxy)methyl]-6-formyl-1,2-dithiin.

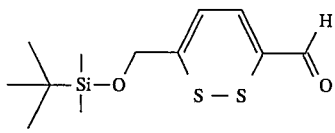

To a solution of 3-[(tert-butyldimethylsilyloxy)methyl]-6-(hydroxymethyl)-1,2-dithiin (U.S. Ser. No. 08/212,096) (600 mg, 2.07 mmol) in THF (25 mL) at 0° C. was added quickly the Dess-Martin periodinane reagent (1.20 g, 2.83 mmol) and the mixture was stirred at 0° C. for 30 min, then at room temperature for another 30 min. Upon completion of the reaction (monitored by TLC), 12 mL of $H_2O$ was added and the mixture was extracted with ether (3×). The combined organics washings were washed with $H_2O$, sodium hydrogen carbonate (3%-soln.), brine, dried ($Na_2SO_4$) and evaporated. Flash chromatography (eluting with hexane/EtOAc 3/1) yielded 560 mg (94%) of the title aldehyde as a dark red, almost purple, crystalline compound.

$R_f$=0.44 (hexane/EtOAc 3/1)

mp=42.5°–43.6° C.

$^1$H NMR (CDCl$_3$)

δ 0.34 (s, 6 H), 1.15 (s, 9 H), 4.55 (s, 2 H), 6.88 (d,J=6.4,1 H), 7.33 (d,J=6.4, 1 H), 9.72 (s, 1 H).

$^{13}$C NMR (CDCl$_3$)

δ −5.5, 18.3, 25.7, 64.6, 123.0, 132.0, 144.2, 148.6, 187.4.

MS (EI)

(m/z ) [M$^+$]: 288

Other peaks: 231 [M-C$_4$H$_9$]$^+$, 201 (100), 173, 125, 97, 75, 73 [C$_3$H$_9$Si]$^+$ HREI: calcd for $C_{12}H_{20}OS_2O_2Si$: 288.0669. Found: 288.0672.

Anal. calcd for $C_{12}H_{20}OS_2O_2Si$: C, 50.0; H, 7.0; S, 22.2. Found: C, 50.1; H, 7.0; S, 22.1.

Example 2

Scale up of 3-[(tert-Butyldimethylsilyloxy)methyl]-6-aldehydyl-1,2-dithiin.

To a solution of 3-[(tert-butyldimethylsilyloxy)methyl]-6-(hydroxymethyl)-1,2-dithiin (U.S. Ser. No. 08/212,096) (3 g, 10.3 mmol) in THF (100 mL) at 0° C. was added quickly the Dess-Martin periodinane reagent (6.0 g, 14.14 mmol) and the mixture was stirred at 0° C. for 30 min, then at room temperature for another 40 min. Upon completion of the reaction (TLC), 60 mL of $H_2O$ was added and the mixture was extracted with ether (3×). The combined organic washings were washed with $H_2O$, sodium hydrogen carbonate (3%-soln.), brine, dried ($Na_2SO_4$) and evaporated. Flash chromatography (eluting with hexane/EtOAc 3/1) yielded 2.44 g (82%) of the title compound as a dark red, crystalline compound.

Example 3

3-(Hydroxymethyl)-6-aldehydyl-1,2-dithiin.

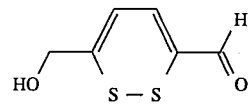

To a solution of the resulting compound of either Examples 1 or 2 (120 mg, 0.416 mmol) in THF (10 mL) at 0° C. was added a previously prepared mixture of tetrabutylammoniumfluoride (TBAF, 2.85 mL, 2.85 mmol; 1M in THF) and acetic acid (1.65 mL, 28.8 mmol) at 0° C. via syringe. The mixture was stirred at 0° C. for 1 h, then at room temperature for another hour. Upon completion (monitored by TLC) the mixture was concentrated to a small volume (3–4 mL), then partitioned between $H_2O$ (36 mL) and EtOAc (48 mL). The aqueous layer was extracted with EtOAc (2×), the combined organics were washed with sodium hydrogen carbonate (3% solution), brine, dried ($Na_2SO_4$) and evaporated. Flash chromatography (eluting with EtOAc) yielded 60 mg (83%) of the title aldehyde as a red oil.

$R_f$=0.54 (EtOAc)

$^1$H NMR (CDCl$_3$)

δ 2.00 (br, 1 H), 4.36 (s, 2 H), 6.70 (d, J=6.0, 1 H), 7.13 (d, J=6.0, 1 H), 9.51 (s, 1 H).

$^{13}$C NMR (CDCl$_3$)

δ 64.3, 124.0, 132.7, 144.1, 148.0, 187.5.

MS (EI)

(m/z) [M$^+$]: 174

Other peaks: 142 [M-S]$^+$, 113 (100), 85.

Example 4

3-[(tert-Butyldimethylsilyloxy)methyl]-6-[ethyl propenoate-3-yl]-1,2-dithiin.

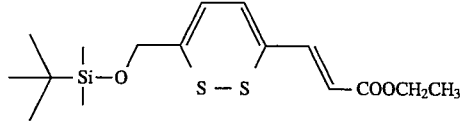

To a solution of triethylphosphonoacetate (131 μL, 0.329 mmol) in THF (5 mL) at −78° C. was added n-butyllithium (66 μL, 0.329 mmol) dropwise and the mixture was stirred for 10 min. This mixture then was cannulated slowly to a solution of the resulting compound of Examples 1 or 2 (100 mg, 0.346 mmol) in THF (5 mL) at −78° C. After 3 hours at −78° C., no reaction had occurred (as monitored by TLC). Therefore another solution of triethylphosphonoacetate (131 μL, 0.329 mmol) in THF (5 mL) at −78° C. and n-BuLi (66 μL, 0.329 mmol) was prepared and added as described above. After another 3 hours of reaction time at −78° C., the mixture was allowed to warm up 0° C., and was stirred at 0° C. for 1 h. At this time the starting material was almost gone (TLC). Na$_2$SO$_4$ (2 mL, 1M in H$_2$O) and H$_2$O (10 mL) was added, the mixture was extracted with ether (4×), and then the combined organics were washed with Na$_2$CO$_3$ (1M), brine, dried (Na$_2$SO$_4$) and evaporated. Flash chromatography (eluting with hexane/EtOAc 3/1) yielded 65 mg (52%) of the title compound as a red oil and 29 mg of a mixture of product and unreacted starting material.

$^1$H NMR (CDCl$_3$)

δ 0.12 (s, 6 H), 0.93 (s, 9 H), 1.32 (t, J =7.2, 3 H), 4.24 (q,J=7.2, 2 H), 4.34 (s, 2 H), 6.25 (d, J=15.2, 1 H), 6.53 (d, J=6.4, 1 H), 6.61 (d, J=6.4, 1 H), 7.39 (d, J=15.2, 1 H).

<sup>13</sup>C NMR (CDCl<sub>3</sub>)

δ −5.4, 14.2, 18.3, 25.7, 60.6, 64.9, 122.6, 124.1, 127.7, 134.0, 141.8, 141.9, 166.5.

MS (EI)

(m/z) [M<sup>+</sup>]: 358

Other peaks: 326 [M-S]<sup>+</sup>, 301 [M-C<sub>4</sub>H<sub>9</sub>]<sup>+</sup>, 269 (100), [M-S-C<sub>4</sub>H<sub>9</sub>]<sup>+</sup>241, 195, 149, 121, 75, 57.

Example 5

3-(Hydroxymethyl)-6-[ethyl propenoate-3-yl]-1,2-dithiin.

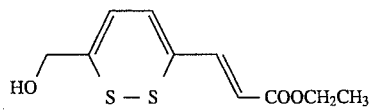

To a solution of 3-[(tert-butyldimethylsilyloxy)methyl]-6-[ethyl propenoate-3-yl]-1,2-dithiin obtained in Example 4 (65 mg, 0.18 mmol) in THF (8 mL) at 0° C. was added a previously prepared mixture of TBAF (1.23 mL, 1.23 mmol; 1M in THF) and acetic acid (0.71 mL) at 0° C. via syringe. The mixture was stirred at 0° C. for 1 h, then at room temperature for another hour. Upon completion (monitored by TLC) the mixture was concentrated to a small volume (2 mL), then partitioned between H<sub>2</sub>O (16 mL) and EtOAc (21 mL). The aqueous layer was extracted with EtOAc (2×), the combined organics were washed with sodium hydrogencarbonate (3%-soln.), brine, dried (Na<sub>2</sub>SO<sub>4</sub>) and evaporated. Flash chromatography (eluting with EtOAc) yielded 35 mg (80%) of the title compound as a red oil.

R<sub>f</sub>=0.41 (EtOAc).

HPLC: PRP-1 column (=polymer reversed phase) from Hamilton, eluting with H<sub>2</sub>O/CH<sub>3</sub>CN 50/50, detecting at 254 nm.

<sup>1</sup>H NMR (CDCl<sub>3</sub>)

δ 1.32 (t, J=7.2, 3 H), 2.08 (s, br, 1 H), 4.25, (q, J=6.8, 2 H), 4.35 (s, 2 H), 6.27 (d, J=15.2, 1 H), 6.56 (d, J =5.6, 1 H), 6.61 (d, J=6.4, 1 H), 7.39 (d, J=15.2, 1 H).

<sup>13</sup>C NMR (CDCl<sub>3</sub>)

δ 14.2, 60.7, 64.5, 123.0, 125.3, 128.5, 133.8, 141.2, 141.7, 166.5.

MS (EI)

(m/z) [M<sup>+</sup>]: 244

Other peaks: 214, 186, 169, 142, 109, 97, 69, 45.

HREI calcd for C<sub>10</sub>H<sub>12</sub>O<sub>3</sub>S<sub>2</sub>: 244.0228. Found: 244.0228.

Example 6

3-[(tert-Butyldimethylsilyloxy)methyl)]-6-[methyl propenoate-3-yl]-1,2-dithiin.

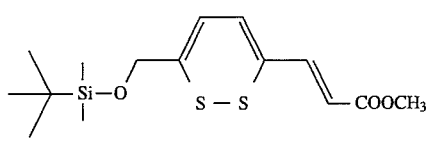

To a solution of trimethylphosphonoacetate (130 μL, 0.90 mmol) in THF (4 mL) at −78° C. was added n-BuLi (360 μL, 0.90 mmol) dropwise and the mixture was stirred for 10 min. This mixture then was cannulated slowly to a solution of the resulting compound of Examples 1 or 2 (130 mg, 0.45 mmol) in THF (8 mL) at −78° C. After 3 hours at −78° C., TLC showed incomplete reaction. The mixture was allowed to warm up 0° C., and was stirred at 0° C. for 1 h. At this time the starting material was almost gone (TLC). Na<sub>2</sub>SO<sub>4</sub> (3 mL, 1M in H<sub>2</sub>O) and H<sub>2</sub>O (5 mL) were added, the mixture was extracted with ether (4×), the combined organics were washed with Na<sub>3</sub>CO<sub>3</sub> (1M), brine, and then dried (Na<sub>2</sub>SO<sub>4</sub>) and evaporated. Flash chromatography (eluting with hexane/ EtOAc 3/1) yielded 132 mg (85%) of the title compound as a red oil.

<sup>1</sup>H NMR (CDCl<sub>3</sub>)

δ 0.00 (s, 6 H), 0.82 (s, 9 H), 3.67 (s, 3 H), 4.23 (s, 2 H), 6.14 (d, J=15.2, 1 H), 6.42 (m, 1 H), 6.50 (d, J=6.4, 1 H), 7.29 (d, J=15.2, 1 H).

<sup>13</sup>C NMR (CDCl<sub>3</sub>)

δ −5.5, 25.7, 51.7, 64.8, 122.0, 124.0, 127.5, 134.1, 141.9, 142.1, 169.9.

MS (EI)

(m/z) [M<sup>+</sup>]: 344

Other peaks: 312, 287, 255 (100), 227, 181, 144, 121, 100, 84, 49.

Example 7

3-(Hydroxymethyl)-6-[methyl propenoate-3-yl]-1,2-dithiin.

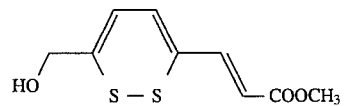

To a solution of the resulting compound of Example 6 (121 mg, 0.35 mmol) in THF (16 mL) at 0° C. was added a previously prepared mixture of TBAF (2.39 mL, 2.39 mmol; 1M in THF) and acetic acid (1.38 mi) at 0° C. via syringe. The mixture was stirred at 0° C. for 1 h, then at room temperature for another hour. Upon completion (as monitored by TLC) the mixture was concentrated to a small volume (3 mL), then partitioned between H<sub>2</sub>O (30 mL) and EtOAc (42 mL). The aqueous layer was extracted with EtOAc (2×), the combined organics were washed with sodium hydrogencarbonate (3%-soln.), brine, dried (Na<sub>2</sub>SO<sub>4</sub>) and evaporated. Flash chromatography (eluting with EtOAc) yielded 70 mg (87%) of the title compound as orange crystals.

R<sub>f</sub>=0.47 (EtOAc).

HPLC: PRP-1 column from Hamilton, eluting with H<sub>2</sub>O/ CH<sub>3</sub>CN 55/45, detecting at 254 nm.

m.p. 80.5°–81° C.

<sup>1</sup>H NMR (CDCl<sub>3</sub>)

δ 1.99 (t, J=6.0, 1 H), 3.70 (s, 3 H), 4.35 (s, 2 H), 6.28 (d, J=15.2, 1 H), 6.56 (d, J=6.4, 1 H), 6.62 (d, J=6.4, 1 H), 7.40 (d, J=15.2, 1 H).

<sup>13</sup>C NMR (CDCl<sub>3</sub>)

δ 51.9, 64.6, 122.6, 125.4, 133.9, 142.0. Remark: not enough sample/transients for quaternary carbons.

MS (EI)

(m/z) [M<sup>+</sup>]: 230 (100)

Other peaks: 200, 169, 153, 137, 121, 97, 69, 59, 45.

HREI calcd for C<sub>9</sub>H<sub>10</sub>O<sub>3</sub>S<sub>2</sub>: 230.0071. Found: 230.0071.

Example 8

3-[(tert-Butyldimethylsilyloxy)methyl]-6-[N-methoxy-iminomethyl]-1,2-dithiin.

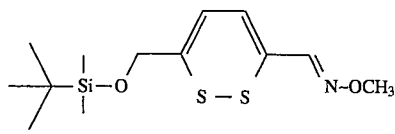

To a solution of the resulting compound of Examples 1 or 2 (105 mg, 0.36 mmol) in glyme (5 mL) was added methoxylamine hydrochloride (30 mg, 0.36 mmol) and pyridine (29 μL, 0.36 mmol). After stirring at room temperature for 5 hours, only a small amount of a potential product was detected by TLC. Therefore another 1 eq. of methoxylamine hydrochloride (30 mg) and 4(–)methylmorpholine (33 μL, 0.36 mmol) were added and the mixture was stirred another 24 h at room temperature. The reaction mixture was then poured onto ice-water, the aqueous layer extracted with ether (3×), then the combined organics washed with 0.5M HCl, brine, dried ($Na_2SO_4$) and evaporated. Flash chromatography (eluting with hexane/EtOAc 5/1) yielded 6 mg (0.019 mmol), of one isomer of the title oxime plus 52 mg (0.164 mmol) of a mixture of both isomers of the title oxime; total yield, 51%. 10 mg (0.029 mmol, 8%) of unreacted starting material was also isolated.

$R_f$=0.52 (hexane/EtOAc 5/1) one isomer.

0.46 (hexane/EtOAc 5/1) other isomer.

$^1$H NMR ($CDCl_3$)

δ 0.11 (s, 6 H), 0.93 (s, 9 H), 3.97 (s, 3 H), 4.32 (s, 2 H), 6.49 (s, 2 H), 7.82 (s, 1 H).

$^{13}$C NMR ($CDCl_3$)

δ –5.4, 18.3, 25.8, 62.5, 64.9, 123.6, 131.8, 139.7, 147.9.

MS (EI)

(m/z) [M$^+$]: 317 (100)

Other peaks: 286 [M-OCH$_3$]$^+$, 260 [M—C=N—OCH$_3$]$^+$, 230, 186, 154, 115, 89, 73, 57, 41.

Example 9

3-(Hydroxymethyl)-6-[N-methoxyiminomethyl]-1,2-dithiin.

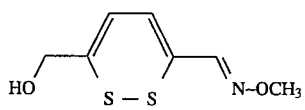

To a solution of both isomers of the resulting compound of Example 8 (52 mg, 0.164 mmol) in THF (5 mL) at 0° C. was added a previously prepared mixture of TBAF (1. 1 2 mL, 1. 1 2 mmol; 1M in THF) and acetic acid (0.65 mL) at 0° C. via syringe. The mixture was stirred at 0° C. for 1 h, then at room temperature for 75 min. Upon completion (as monitored by TLC) the mixture was concentrated to a small volume (2 mL), then partitioned between H$_2$O (15 mL) and EtOAc (20 mL). The aqueous layer was extracted with EtOAc (2×), the combined organics were washed sequentially with sodium hydrogencarbonate (3%-soln.) and brine, and then dried (Na$_2$SO$_4$) and evaporated. Flash chromatography (eluting with hexane/EtOAc 1/1) yielded 30 mg (90%) of the title oxime as orange crystals.

0.37 (hexane/EtOAc 1/1)

HPLC: PRP-1 column from Hamilton, eluting with H$_2$O/CH$_3$CN 60/40, detecting at 254 nm.

mp 48.4°–49.3° C.

$^1$H NMR (CDCl$_3$)

δ 3.97 (s, 3 H), 4.32 (s, 2 H), 6.50 (m, 2 H), 7.82 (s, 1 H).

$^{13}$C NMR (CDCl$_3$)

δ 62.6, 64.6, 124.9, 126.9, 131.6, 139.0, 147.7.

MS (EI)

(m/z) [M$^+$]: 203 (100)

Other peaks: 173, 142, 114, 95, 84, 69, 58, 45.

HREI calcd for $C_7H_9NO_2S_2$: 203.0073. Found: 203.0075.

Example 10

3-[tert-Butyldimethylsilyloxymethyl]-6-[N-hydroxyiminomethyl]-1,2-dithiin.

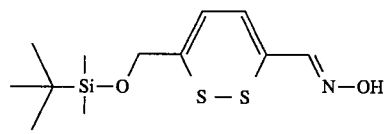

To a solution of the resulting compound of Examples 1 or 2 (690 mg, 2.39 mmol) in glyme (24 mL) at room temperature was added pyridine (203 μL, 2.51 mmol), followed by hydroxylamine hydrochloride (175 mg, 2.51 mmol) After stirring at room temperature for 5 h via mechanical stirrer, another 105 mol % of pyridine (203, 4, 2.51 mmol) and hydroxylamine hydrochloride (175 mg) were added and the mixture was stirred for 17 h at room temperature. Upon completion of the reaction, the mixture was poured onto ice-water, diluted with ether and separated. The aqueous layer was extracted with ether (3×), the combined organics washed with 0.4M HCl, brine, and then dried (MgSO$_4$) and evaporated. Flash chromatography (eluting with hexane/EtOAc 3/1) yielded 602 mg (1.98 mmol, 83%) of the title compound. R$_f$ 0.38 (hexane/EtOAc 3/1).

$^1$H NMR (CDCl$_3$)

δ 0.12 (s, 6 H), 0.93 (s, 9 H), 1.7 (br, 1 H), 4.34 (s, 2 H), 6.54 (m, 2 H), 7.90 (s, 1 H).

$^{13}$C NMR (CDCl$_3$)

δ –5.4, 18.3, 25.8, 64.9, 123.5, 125.9, 132.2, 140.2, 149.3.

MS (EI)

(m/z) [M$^+$]: 303

Other peaks: 286, 246, 214 (100), 173, 142, 122, 97, 75, 57, 45.

Example 11

3-(Hydroxymethyl)-6-[N-hydroxyiminomethyl]-1,2-dithiin.

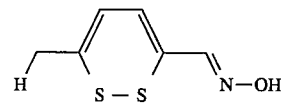

To a solution of the resulting compound of Example 10 (602 mg, 1.98 mmol) in THF (40 mL) at 0° C. was added a previously prepared mixture of TBAF (5.94 mL, 5.94 mmol; 1M in THF) and acetic acid (3.40 mL, 59.4 mmol) at 0° C. via syringe. The mixture was stirred at 0° C. for 30 min, then at room temperature for 3 h. Upon completion of the reaction (as monitored by TLC) the mixture was concentrated to a small volume (5 mL), then partitioned between H₂O (70 mL) and EtOAc (140 mL). The aqueous layer was extracted with EtOAc (2×), the combined organics were washed with sodium hydrogencarbonate (3%-soln.), brine, dried (Na₂SO₄) and evaporated. Chromatography (applied to the column as an adsorbate on silica gel, eluting with hexane/EtOAc 1/1) yielded 289 mg (1.53 mmol, 77%) of the title compound as orange crystals.

R$_f$=0.29 (hexane/EtOAc 1/1).

mp 126.8°–127.3° C.

¹H NMR (DMSO-d₆)

δ 4.13 (d, J=5.6, 2 H), 5.47 (m, 1 H), 6.52 (dd, d, J=6.4, 1.2, 1 H), 6.70 (d, J=6.8, 1 H), 8.00 (s, 1 H), 11.67 (s, 1 H).

¹³C NMR (DMSO-d₆)

δ 63.3, 124.1, 126.7, 130.8, 138.62, 148.0.

MS (EI)

(m/z) [M⁺]: 189 (100)

Other peaks: 159.

HREI calcd for C₆H₇NO₂S₂: 188.9924. Found: 188.9918.

Anal. calcd for C₆H₇NO₂S₂: C, 38.08; H, 3.73; N, 7.40; S, 33.88. Found: C, 38.31; H, 3.83; N, 7.14; S, 33.86.

Example 12

3-[(tert-Butyldimethylsilyloxy)methyl]-6-[2-cyanoethene-1-yl]-1,2-dithiin.

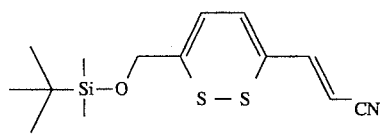

NaNH₂ (44 mg, 1.067 mmol) was weighed quickly into an oven-dried flask, suspended in THF (4 mL) and cooled to −78° C. To this suspension, (EtO)₂P(O)CH₂CN (173 μL 1.067 mmol) was added dropwise and stirred for 10 min at −78° C. This mixture then was cannulated to a solution of the resulting compound of Examples 1 or 2 (154 mg, 0.533 mmol) in THF (5 mL), at −78° C. The reaction was stirred at −78° C. for 3h, then at 0° C. for 90 min. At this time the starting material was almost gone (TLC). Na₂SO₄ (5 mL, 1M in H₂O) and H₂O (10 mL) was added, the mixture then being extracted with ether (4×), the combined organics washed with Na₂CO₃ (1M), brine, dried (Na₂SO₄) and evaporated. Chromatographies (eluting with hexane/EtOAc 3/1, then separation of mixed fractions by eluting with hexane/EtOAc 4/1) yielded a total of 91 mg (55%) of the title compound. Another 5 mg (0,033 mmol, 6%) unreacted starting material was also isolated.

R$_f$=0.51 (hexane/EtOAc 4/1).

¹H NMR (CDCl₃)

δ 0.10 (s, 6 H), 0.92, (s, 9 H), 4.36 (s, 2 H), 5.76 (d, J=16.0, 1 H), 6.59 (m, 2 H), 7.12 (d, J=16.0, 1 H).

¹³C NMR (CDCl₃)

δ −5.4, 18.3, 25.7, 64.8, 100.4, 117.7, 123.8, 125.8, 134.8, 144.2, 147.3.

MS (EI)

(m/z) [M⁺]: 311

Other peaks: 245, 224 (100) [M-C₆H₁₅]⁺, 148, 69.

Example 13

3-(Hydroxymethyl)-6-[2-cyanoethene-1-yl]-1,2-dithiin.

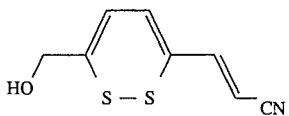

To a solution of the resulting compound of Example 12 (54 mg, 0.173 mmol) in THF (5 mL) at 0° C. was added a previously prepared mixture of TBAF (1.176 mL, 1.176 mmol; 1M in THF) and acetic acid (0.68 mL) at 0° C. via syringe. The mixture was stirred at 0° C. for 1 h, then at room temperature for 1 h. Upon completion (TLC) the mixture was concentrated to a small volume (1 mL), then partitioned between H₂O (16 mL) and EtOAc (22 mL). The aqueous layer was extracted with EtOAc (2×), the combined organics were washed with sodium hydrogencarbonate (3%-soln.) and brine, and then dried (Na₂SO₄) and evaporated. Chromatography (eluting with hexane/EtOAc 1/1) yielded 32 mg (94%) of the title compound as an orange powder.

0.31 (hexane/EtOAc 1/1)

mp 96.6°–97.9° C.

¹H NMR (CDCl₃)

δ 2.06 (br, 1 H), 4.37 (s, 2 H), 5.78 (d, J=16.0, 1 H), 6.60, (s, 2 H), 7.13 (d, J=15.6, 1 H).

¹³C NMR (CDCl₃)

δ 64.4, 100.8, 117.6, 125.0, 126.5, 134.6, 143.5, 147.2.

MS (EI)

(m/z) [M+]: 197

Other peaks: 167 (100) [M-CN]+, 136, 122, 85, 43.

HREI calcd for C₈H₇NOS₂: 196.9971. Found: 196.9969.

Example 14

3-[(tert-Butyldimethylsilyloxy)methyl]-6-cyano-1,2-dithiin.

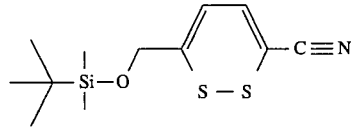

To a solution of the resulting compound of Example 10 (71 mg, 0.234 mmol) in CH₂Cl₂ (5 mL) at room temperature was added BDDC (139 mg, 0.515 mmol), prepared by the procedure of Rapoport (Gibson, F. S.; Park, M. S.; Rapoport, H. *J. Org. Chem.* 1994, 59, 7503) followed by Cu(I)Cl (51 mg, 0.515 mmol) and the mixture was stirred for 5h. Upon completion of the reaction (TLC), the mixture was diluted with EtOAc, washed with 0.2M HCl, sodium hydrogencarbonate (3%-soln.) and brine, and then dried (Na₂SO₄) and evaporated. Chromatography (eluting with hexane/EtOAc 4/1) yielded 45 mg (68%) of the title compound as a dark red oil.

R$_f$=0.39 (hexane/EtOAc 4/1).

¹H NMR (CDCl₃)

δ 0.12 (s, 6 H), 0.93 (s, 9 H), 4.33 (s, 2 H), 6.57 (m, 1 H), 6.98 (d, J=6.4, 1 H).

¹³C NMR (CDCl₃)

δ −5.5, 18.3, 25.7, 64.5, 98.1, 114.9, 122.9, 142.2, 147.2.

MS (EI)

(m/z) [M$^+$]: 285

Other peaks: 228, 196 (100), 166, 122, 73.

Example 15

3-(Hydroxymethyl)-6-cyano-1,2-dithiin.

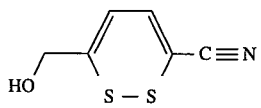

To a solution of the resulting compound of Example 14 in THF (5 mL) at 0° C. was added a previously prepared mixture of tetrabutylammoniumfluoride (TBAF, 1.02 mL, 1.02 mmol; 1M in THF) and acetic acid (0.59 mL) at 0° C. via syringe. The mixture was stirred at 0° C. for 1 h, then at room temperature for another hour. Upon completion of the reaction (TLC) the mixture was concentrated to a small volume (1 mL), then partitioned between H$_2$O (13 mL) and EtOAc (18 mL). The aqueous layer was extracted with EtOAc (2×), the combined organics were washed with sodium hydrogencarbonate (3%-soln.) and brine, and then dried (Na$_2$SO$_4$) and evaporated. Chromatography (eluting with hexane/EtOAc 1/1) yielded 23 mg (90%) of the title compound as a dark red oil.

0.30 (hexane/EtOAc 1/1).

$^1$H NMR (CDCl$_3$)

2.16 (m, 1 H), 4.41 (d, J=4.4, 2 H), 6.66 (d, J=6.4, 1 H), 7.05 (d, J=6.4, 1 H).

$^{13}$C NMR (CDCl$_3$)

δ 64.1, 98.9, 114.7, 123.9, 142.2, 146.6.

MS (EI)

(m/z) [M$^+$]: 171

Other peaks: 153, 141 (100), 114, 77.

HREI calcd for C$_6$H$_5$NOS$_2$: 170.9812. Found: 170.9813.

Example 16

3,6-Bis(formyl)-1,2-dithiin.

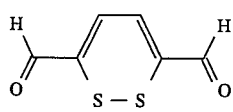

To a solution of 3,6-bis(hydroxymethyl)-1,2-dithiin (U.S. Ser. No. 08/212,096 and Koreeda et al., Synlett, 1994, 201) (844 mg, 4.78 mmol) in THF (50 mL) at 0° C. was added quickly the Dess-Martin periodinane reagent (4.78 g, 11.49 mmol) and the mixture was stirred at 0° C. for 30 min, then at room temperature for another 40 min. Upon completion of the reaction, H$_2$O (25 mL) was added and the mixture was extracted with ether (3×). The combined organics were washed with H$_2$O, sodium hydrogencarbonate (3%-soln.) and brine, and then dried (MgSO$_4$) and evaporated. Chromatography (eluting with hexane/EtOAc 1/1) yielded 820 mg (100%) of the title bis aldehyde as a deep purple, crystalline compound.

0.31 (hexane/EtOAc 1/1).

mp 62.0°–63.1° C.

$^1$H NMR (CDCl$_3$)

δ 7.25 (s, 2 H), 9.56 (s, 2 H).

$^{13}$C NMR (CDCl$_3$)

δ 141.4, 142.0, 186.4.

MS (EI)

(m/z) [M$^+$]: 172

Other peaks: 140 (100) [M-S]$^+$, 116, 71.

HREI Calcd for C$_6$H$_4$O$_2$S$_2$: 171.9654. Found: 171.9653.

Anal. calcd for C$_6$H$_4$O$_2$S$_2$: C, 41.84; H, 2,34. Found: C, 41.84; H, 2.61.

Example 17

3,6-[Bis(N-hydroxyiminomethyl)]-1,2-dithiin.

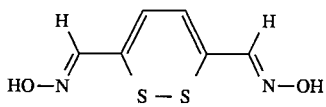

To a solution of the resulting compound of Example 16 (1.10 g, 6.39 mmol) in glyme (40 mL) at room temperature was added pyridine (1.08 mL, 13.41 mmol), followed by hydroxylamine hydrochloride (932 mg, 13.41 mmol). Upon completion of the reaction (5 h, mechanical stirring, monitored by TLC), the mixture was poured onto ice-water (40 mL), diluted with ether and separated. The aqueous layer was extracted with ether (3×), the combined organics were washed with 0.4M HCl and brine, and then dried (MgSO$_4$) and evaporated. Chromatography (applied to the column as an adsorbate, eluting with hexane/EtOAc 2/1 (1000 mL), hexane/EtOAc 1/1 (200 mL), then EtOAc (200 mL)) yielded 574 mg (2.84 mmol, 44%) of the title compound.

R$_f$=0.25 (hexane/EtOAc 2/1).

mp color change from red to brown at 173° C., melting at 216.5°–216.7° C.

$^1$H NMR (DMSO-d$_6$)

δ 6.85 (s, 2 H), 8.05 (s, 2 H), 11.86 (s, 2 H).

$^{13}$H NMR (DMSO-d$_6$)

129.6, 130.7, 148.0.

MS (EI)

(m/z) [M$^+$]: 202

Other peaks: 170 [M-S]$^+$, 159 (100), 136, 109.

HREI calcd for C$_6$H$_6$N$_2$O$_2$S$_2$: 201.9875. Found: 201.9871

Example 18

3,6-Bis[N-methoxyiminomethyl]-1,2-dithiin.

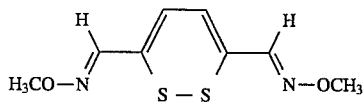

To a solution of the resulting compound of Example 16 (820 mg, 4.76 mmol) in glyme (30 mL) at rt was added pyridine (845 μL, 10.47 mmol), followed by methoxylamine hydrochloride (875 mg, 10.47 mmol). Upon completion of the reaction (5 h, mechanical stirring, monitored by TLC), the mixture was poured onto ice-water (30 mL), diluted with ether and separated. The aqueous layer was extracted with ether (3×), the combined organics were washed sequentially with 0.4M HCl and brine, and then dried (MgSO$_4$) and evaporated. Chromatography (eluting with hexane/EtOAc 3/1) yielded 528 mg (2.29 mmol, 48%) of the title compound. Another 323 mg (1.402 mmol, 29%) of a mixture of the title bis oxime and another diastereoiseric bis oxime was isolated as well.

R$_f$=0.39 (hexane/EtOAc 3/1).

mp 133.2°–134.1° C.

$^1$H NMR (CDCl$_3$)

δ 3.99 (s, 6 H), 6.57 (s, 2 H), 7.83 (s, 2 H).

$^{13}$C NMR (CDCl$_3$)

δ 62.8, 131.1, 147.5.

MS (EI)

(m/z) [M$^+$]: 230

Other peaks: 198 [M-S]$^+$, 173 (100) [M—CN—OCH$_3$]$^+$, 144, 69.

HREI calcd for C$_8$H$_{10}$N$_2$O$_2$S$_2$: 230.0187. Found: 230.0184.

6.3 DISINFECTANT OR CLEANING COMPOSITIONS COMPRISING A 1,2-DITHIIN COMPOUND

Example 19

Approximately 1 mL of a composition containing 25% isopropyl alcohol, 1% sodium dodecylsulfate, 0.01% 3-(hydroxymethyl)-6-cyano-1,2-dithiin and 73.99% distilled water is applied to a rag, sponge or mop. The floor of a bathroom which was used by a person having a fungal infection and is thus contaminated with the fungus is wiped with the rag, sponge or mop containing the above composition. The resulting bathroom floor is now disinfected and ready for use. The resulting floor may optionally be washed with detergent prior to use, if desired.

Example 20

Approximately 10 mL of a composition containing 25% isopropyl alcohol, 1% sodium dodecylsulfate, 0.01% 3,6-[bis(O-methylhydroxyforminimyl)]-1,2-dithiin and 73.99% distilled water are poured into a laboratory flask which contains a live culture of *Candida albicans* fungus. The flask is swerled several times and allowed to sit at room temperature for a short period of time. The contents of the flask are discarded, the flask is rinsed with sterile water and the flask is allowed to air dry under aseptic conditions. The resulting flask is now disinfected and ready for re-use. The resulting flask may optionally be washed with soap and water prior to re-use, if desired.

7. EXAMPLE: ANTIFUNGAL EFFECTS OF 1,2-DITHIIN COMPOUNDS

The following experiments demonstrate that the 1,2-dithiin compounds of the present invention produce a significant and consistent antifungal effect as determined in an in vitro assay.

The antifungal activities of representative 1,2-dithiin compounds listed below were determined in vitro using three fungal cultures: *Candida albicans* ATCC10259 (CA), *Cryptococcus neoformans* ATCC36556 (CN), and *Aspergillus fumigatus* ATCC13073 (AF). The the minimum inhibitory concentration (MIC) for each 1,2-dithiin compound is shown below in Table I.

Additionally, two 1,2-dithiin compounds, 3-(hydroxymethyl)-6-[N-hydroxyiminomethyl]-1,2-dithiin and 3,6-[bis(N-hydroxyiminomethyl)]-1,2-dithiin, were chosen as compounds representative of the 1,2-dithiin class to be tested against a variety of fungi: *Candida albicans* A-26 (A-26), *Candida albicans* B311 (B311), *Candida krusei* GK7831 (CK), *Candida parapsilosis* CP18 (CP), *Candida tropicalis* 1525 (CT), *Cryptococcus neoformans* MI-106 (MI-106), *Aspergillus fumigatus* WM-1 (WM-1) and *Trichophyton rubrum* ATCC18762 (TR). The minimum inhibitory concentration (MIC) for 3-(hydroxymethyl)-6-[N-hydroxyiminomethyl]-1,2-dithiin and 3,6-[bis(N-hydroxyiminomethyl)]-1,2-dithiin are shown below in Table II.

The method used to determine in vitro antifungal activity is discussed in McGinnis, M. R., *Laboratory Handbook of Medical Mycology*, Academic Press, New York, London, p. 661 (1980); and Drouget, E.; Dupont, B.; Improvist, L.; Vivian, M. A.; and Tortorano, A. M.; "Disc Agar Diffusion and Microplate Automatized Techniques for In Vitro Evaluation of Antifungal Agents on Yeast and Sporulated Pathogenic Fungi" in In Vitro and In Vivo Evaluation of Antifungal Agents, Eds. lwata, K. and Vanden Bossche, H., Elsevier Science Publishers, New York, Oxford, p. 303 (1986).

The abbreviations used for the various fungi in Tables I and II are as follows:

| Fungi | Abbreviation |
| --- | --- |
| *Candida albicans* ATCC10259 | (CA) |
| *Cryptococcus neoformans* ATCC36556 | (CN) |
| *Aspergillus fumigatus* ATCC13073 | (AF) |
| *Candida albicans* A-26 | (A-26) |
| *Candida albicans* B311 | (B311) |
| *Candida krusei* GK7831 | (CK) |
| *Candids parapsilosis* CP 18 | (CP) |
| *Candida topicalis* 1525 | (CT) |
| *Cryptococcus neoformans* MI-106 | (MI-106) |
| *Aspergillus fumigatus* WM-1 | (WM-1) |
| *Trichophyton rubrum* ATCC18762 | (TR) |

TABLE I

Minimum Inhibitory Concentration of Representative 1,2-Dithiin Compounds on CA, CN and AF Fungal Cultures

| Dithiin Derivative | MIC (µg/mL) | | |
| --- | --- | --- | --- |
| | CA | CN | AF |
| 3-(Hydroxymethyl)-6-formyl-1,2-dithiin | 12.5 | 6.3 | 25 |
| 3-(Hydroxymethyl)-6-[ethyl propenoate-3-yl]-1,2-dithiin | 12.5 | 6.3 | 25 |
| 3-(Hydroxymethyl)-6-[methyl propenoate-3-yl]-1,2-dithiin | 6.3 | 6.3 | 6.3 |
| 3-(Hydroxymethyl)-6-[N-methoxyiminomethyl]-1,2-dithiin | 6.3 | 6.3 | 6.3 |
| 3-(Hydroxymethyl)-6-[N-hydroxyiminomethyl]1,2-dithiin | 1.6 | 1.6 | 1.6 |
| 3-(Hydroxymethyl)-6-[2-cyanoethene-1-yl]-1,2-dithiin | 12.5 | 3.1 | 6.3 |
| 3-(Hydroxymethyl)-6-cyano-1,2-dithiin | 0.8 | 0.8 | 0.8 |
| 3-6-Bis(formyl)-1,2-dithiin | 1.6 | 1.6 | 6.3 |
| 3,6-[Bis(N-hydroxyiminomethyl)]-1,2-dithiin | 0.1 | 0.8 | 0.4 |
| 3,6-[Bis(N-methoxyiminomethyl)]-1,2-dithiin | 0.8 | 1.6 | 6.3 |

TABLE II

Minimum Inhibitory Concentration of 3-(Hydroxymethyl)-6-[N-hydroxyiminomethyl]-1,2-dithiin and 3,6-[Bis(N-hydroxyiminomethyl)]-1,2-dithiin of Representative Fungal Cultures

| Dithiin Derivative | MIC (μg/mL) | | | | | | | |
|---|---|---|---|---|---|---|---|---|
| | A-26 | B311 | CK | CP | CT | MI-106 | WM-1 | TR |
| 3-(Hydroxymethyl)-6-[N-hydroxyiminomethyl]-1,2 dithiin | 1.6 | 1.6 | 6.3 | 3.1 | 6.3 | 1.6 | 1.6 | 0.8 |
| 3,6-[Bis(N-hydroxyiminomethyl)]-1,2 dithiin | 0.2 | 0.1 | 6.3 | 0.2 | 1.6 | 1.6 | 0.2 | 0.05 |

The results shown in Tables I and II clearly demonstrate that the novel 1,2-dithiin compounds of the present invention possess antifungal activity against a wide variety of fungal cultures.

The present invention is not to be limited in scope by the specific embodiments disclosed in the examples which are intended as illustrations of a number of aspects of the invention and any embodiments which are functionally equivalent are within the scope of this invention. Indeed, various modifications of the invention in addition to those shown and described herein will become apparent to those skilled in the art and are intended to fall within appended claims.

A number of references have been cited, the entire disclosures of which are incorporated herein by reference.

What is claimed is:

1. A compound having the formula I:

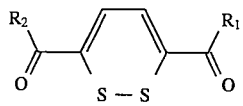

and pharmaceutically acceptable salts thereof, wherein:

$R_1$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl; and $R_2$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl, with the proviso that $R_1$ and $R_2$ are not simultaneously hydrogen.

2. A compound having the formula II:

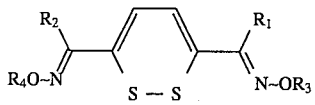

and pharmaceutically acceptable salts thereof, wherein:

$R_1$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_2$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_3$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

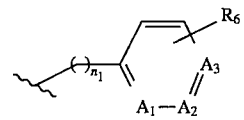

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_1$, $A_2$, and $A_3$ are independently N, or C—H;

$R_6$ is selected from the group consisting of hydrogen, —OH, halogen, —OCH$_3$, —SH, —S(O)n$_2$CH$_3$, and —NH$_2$;

$n_1$=0–2;

$n_2$=0–2;

$R_4$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

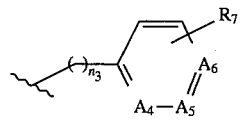

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, —OH, halogen, —OCH$_3$, —SH, —S(O)n$_4$CH$_3$, and —NH$_2$;

$n_3$=0–2

$n_4$=0–2; and with the proviso that $R_1$ and $R_2$ are not simultaneously —OH.

3. A compound having the formula III:

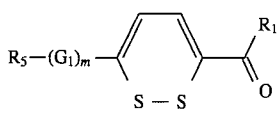

and pharmaceutically acceptable salts thereof, wherein:

$R_1$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$G_1$ is selected from the group consisting of a $C_1$–$C_{10}$ alkyl or branched alkyl group and a $C_3$–$C_{10}$ cycloalkyl group;

m=0–1;

$R_5$ is selected from the group consisting of hydrogen, azido, cyano, formyl, halogen, $OR_{10}$, $SR_{11}$, $COR_{12}$, $CR_2(=NOR_4)$ and $CO_2R_{13}$;

$R_{10}$ is selected from the group consisting of hydrogen, a $C_1$–$C_{10}$ alkyl group, a $C_3$–$C_{10}$ cycloalkyl group, an acyl radical of the type

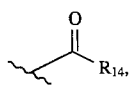

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, OH, $COOCH_2CH_3$, $OCH_3$, $OCH_2CH_3$, $NO_2$, $CF_3$, $C_1$–$C_6$ alkyl, $NH_2$, and OAc;

$R_{14}$ is selected from the group consisting of methyl, ethyl, 1-(methyl)ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and a 5–6 membered ring heteroaryl radical being optionally substituted with one or more halogen, $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{11}$ is selected from the group consisting of hydrogen, a $C_1$–$C_{10}$ alkyl group, a $C_3$–$C_{10}$ cycloalkyl group, an acyl radical of the type

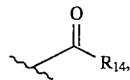

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{12}$ is selected from the group consisting of methyl, ethyl, 1-(methyl)ethyl; n-propyl, an alkyl radical of 4 to 10 carbon atoms, a $C_3$–$C_8$ cycloalkyl group, phenyl and benzyl; said phenyl and benzyl groups being optionally substituted with one or more halogen, $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$; and $R_{13}$ is selected from the group consisting of hydrogen, methyl, ethyl, 1-(methyl)ethyl, n-propyl, an alkyl radical of 4 to 10 carbon atoms, a $C_3$–$C_8$ cycloalkyl group, phenyl and benzyl; said phenyl and benzyl groups being optionally substituted with one or more $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl, $NH_2$ and halogen;

with the proviso that when m=0, $R_5$ is selected from the group consisting of cyano, formyl, $COR_{12}$, $CO_2R_{13}$, and $CR_2(=NOR_4)$, except that when $R_1$ is hydrogen and m=0, $R_5$ is not formyl;

wherein $R_2$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

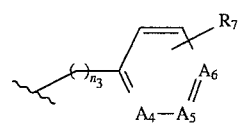

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, —OH, halogen, —$OCH_3$, —SH, —$S(O)n_4CH_3$, and —$NH_2$;

$n_3$=0–2; and $n_4$=0–2.

4. A compound having the formula IV:

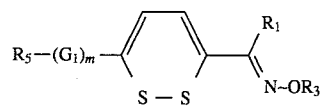

and pharmaceutically acceptable salts thereof, wherein:

$R_1$ is selected from the group consisting of hydrogen, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_3$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

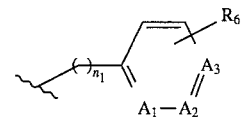

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_1$, $A_2$, and $A_3$ are independently N, or C—H;

$R_6$ is selected from the group consisting of hydrogen, —OH, halogen, —$OCH_3$, —SH, —$S(O)n_2CH_3$, and —$NH_2$;

$n_1$=0–2;

$n_2 = 0-2$;

$G_1$ is selected from the group consisting of a $C_1$–$C_{10}$ alkyl or branched alkyl group and a $C_3$–$C_{10}$ cycloalkyl group;

$m = 0-1$;

$R_5$ is selected from the group consisting of hydrogen, azido, cyano, formyl, halogen, $OR_{10}$, $SR_{11}$, $COR_{12}$, $CR_2(=NOR_4)$ and $CO_2R_{13}$;

$R_{10}$ is selected from the group consisting of hydrogen, a $C_1$–$C_{10}$ alkyl group, a $C_3$–$C_{10}$ cycloalkyl group, an acyl radical of the type

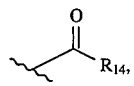

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, OH, $COOCH_2CH_3$, $OCH_3$, $OCH_2CH_3$, $NO_2$, $CF_3$, $C_1$–$C_6$ alkyl, $NH_2$, and OAc;

$R_{14}$ is selected from the group consisting of methyl, ethyl, 1-(methyl)ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and a 5–6 membered ring heteroaryl radical being optionally substituted with one or more $SCH_3$, COOH, halogen, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{11}$ is selected from the group consisting of hydrogen, a $C_1$–$C_{10}$ alkyl group, a $C_3$–$C_{10}$ cycloalkyl group, an acyl radical of the type

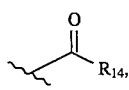

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{12}$ is selected from the group consisting of methyl, ethyl, 1-(methyl)ethyl; n-propyl, an alkyl radical of 4 to 10 carbon atoms, a $C_3$–$C_8$ cycloalkyl group, phenyl and benzyl; said phenyl and benzyl groups being optionally substituted with one or more $SCH_3$, COOH, $COOCH_3$, $COOCH_2CH_3$, OH, OAc, $OCH_3$, $OCH_2CH_3$, $NO_2$, $CF_3$, $C_1$–$C_6$ alkyl and $NH_2$, halogen; and $R_{13}$ is selected from the group consisting of hydrogen, methyl, ethyl, 1-(methyl)ethyl, n-propyl, an alkyl radical of 4 to 10 carbon atoms, a $C_3$–$C_8$ cycloalkyl group, phenyl and benzyl; said phenyl and benzyl groups being optionally substituted with one or more halogen, $SCH_3$, COOH, $COOCH_3$, $COOCH_2CH_3$, OH, OAc, $OCH_3$, $OCH_2CH_3$, $NO_2$, $NH_2$, $CF_3$ and $C_1$–$C_6$ alkyl;

with the proviso that when $m=0$, $R_5$ is selected from the group consisting of cyano, formyl, $COR_{12}$, $CO_2R_{13}$, and $CR_2(=NOR_4)$, wherein $R_2$ is selected from the group consisting of hydrogen, —OH, a $C_1$–$C_{10}$ alkyl group, a $C_2$–$C_{10}$ alkenyl group and a $C_2$–$C_{10}$ alkynyl group; said alkyl, alkenyl or alkynyl groups being optionally substituted with one or more groups selected from the group consisting of $C_1$–$C_6$ alkyl and phenyl;

$R_4$ is selected from the group consisting of hydrogen, a $C_1$–$C_{10}$ alkyl group, a $C_2$–$C_{10}$ alkenyl group, a $C_2$–$C_{10}$ alkynyl group, phenyl, benzyl and a heteroaromatic radical of the type:

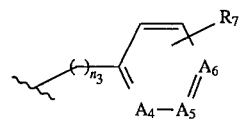

said $C_1$–$C_{10}$ alkyl, $C_2$–$C_{10}$ alkenyl, $C_2$–$C_{10}$ alkynyl, phenyl and benzyl groups being optionally substituted with one or more groups selected from the group consisting of $C_1$–$C_6$ alkyl and phenyl;

$A_4$, $A_5$, and $A_6$ are independently N, or C—H;

$R_7$ is selected from the group consisting of hydrogen, halogen, —OH, —$OCH_3$, —SH, —$S(O)n_4CH_3$, and —$NH_2$; and $n_3 = 0-2$; and $n_4 = 0-2$.

5. A compound of formula V:

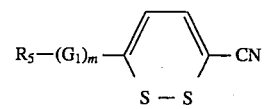

and pharmaceutically acceptable salts thereof, wherein:

$G_1$ is selected from the group consisting of a $C_1$–$C_{10}$ alkyl or branched alkyl group and a $C_3$–$C_{10}$ cycloalkyl group;

$m = 0-1$;

$R_5$ is selected from the group consisting of hydrogen, azido, cyano, formyl, halogen, $OR_{10}$, $SR_{11}$, $COR_{12}$, $CR_2(=NOR_4)$ and $CO_2R_{13}$;

$R_{10}$ is selected from the group consisting of hydrogen, a $C_1$–$C_{10}$ alkyl group, a $C_3$–$C_{10}$ cycloalkyl group, an acyl radical of the type

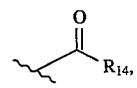

phenyl, benzyl and a 5–6 membered heteroaryl ring; said phenyl, benzyl and 5–6 membered heteroaryl ring being optionally substituted with one or more halogen, $SCH_3$, COOH, $COOCH_3$, OH, $COOCH_2CH_3$, $OCH_3$, $OCH_2CH_3$, $NO_2$, $CF_3$, $C_1$–$C_6$ alkyl, $NH_2$, and OAc;

$R_{14}$ is selected from the group consisting of methyl, ethyl, 1-(methyl) ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and a 5–6 membered ring heteroaryl radical being optionally substituted with one or more $SCH_3$, COOH, halogen, $COOCH_3$, $COOCH_2CH_3$, OH, OAc, $OCH_3$, $OCH_2CH_3$, $NO_2$, $CF_3$, $C_1$–$C_6$ alkyl and $NH_2$;

$R_{11}$ is selected from the group consisting of hydrogen, a $C_1$–$C_{10}$ alkyl group, a $C_3$–$C_{10}$ cycloalkyl group, an acyl radical of the type

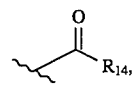

phenyl, benzyl and a 5–6 membered heteroaryl ring; said phenyl, benzyl and 5–6 membered heteroaryl ring being optionally substituted with one or more halogen, SCH$_3$, COOH, COOCH$_3$, COOCH$_2$CH$_3$, OH, OAc, OCH$_3$, OCH$_2$CH$_3$, NO$_2$, CF$_3$, C$_1$–C$_6$ alkyl and NH$_2$;

R$_{12}$ is selected from the group consisting of methyl, ethyl, 1-(methyl)ethyl; n-propyl, an alkyl radical of 4 to 10 carbon atoms, a C$_3$–C$_8$ cycloalkyl group, phenyl and benzyl; said phenyl and benzyl groups being optionally substituted with one or more SCH$_3$, COOH, COOCH$_3$, COOCH$_2$CH$_3$, OH, OAc, OCH$_3$, OCH$_2$CH$_3$, NO$_2$, CF$_3$, C$_1$–C$_6$ alkyl and NH$_2$, halogen; and R$_{13}$ is selected from the group consisting of hydrogen, methyl, ethyl, 1-(methyl)ethyl, n-propyl, an alkyl radical of 4 to 10 carbon atoms, a C$_3$–C$_8$ cycloalkyl group, phenyl and benzyl; said phenyl and benzyl groups being optionally substituted with one or more halogen, SCH$_3$, COOH, COOCH$_3$, COOCH$_2$CH$_3$, OH, OAc, OCH$_3$, OCH$_2$CH$_3$, NO$_2$, NH$_2$, CF$_3$ and C$_1$–C$_6$ alkyl;

with the proviso that when m=0, R$_5$ is selected from the group consisting of formyl, COR$_{12}$, CO$_2$R$_{13}$, and CR$_2$(=NOR$_4$), wherein R$_2$ is selected from the group consisting of hydrogen, —OH, a C$_1$–C$_{10}$ alkyl group, a C$_2$–C$_{10}$ alkenyl group and a C$_2$–C$_{10}$ alkynyl group; said alkyl, alkenyl or alkynyl groups being optionally substituted with one or more groups selected from the group consisting of C$_1$–C$_6$ alkyl and phenyl;

R$_4$ is selected from the group consisting of hydrogen, a C$_1$–C$_{10}$ alkyl group, a C$_2$–C$_{10}$ alkenyl group, a C$_2$–C$_{10}$ alkynyl group, phenyl, benzyl and a heteroaromatic radical of the type:

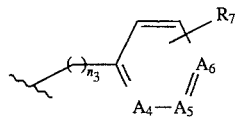

said C$_1$–C$_{10}$ alkyl, C$_2$–C$_{10}$ alkenyl, C$_2$–C$_{10}$ alkynyl, phenyl and benzyl groups being optionally substituted with one or more groups selected from the group consisting of C$_1$–C$_6$ alkyl and phenyl;

A$_4$, A$_5$, and A$_6$ are independently N, or C—H;

R$_7$ is selected from the group consisting of hydrogen, —OH, halogen, —OCH$_3$, —SH, —S(O)n$_4$CH$_3$, and —NH$_2$; and n$_3$=0–2; and n$_4$=0–2.

6. A compound of formula VI:

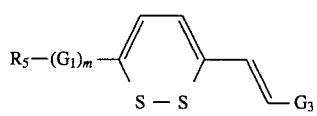

and pharmaceutically acceptable salts thereof, wherein:

G$_1$ is selected from the group consisting of a C$_1$–C$_{10}$ alkyl or branched alkyl group and a C$_3$–C$_{10}$ cycloalkyl group;

m=0–1;

R$_5$ is selected from the group consisting of hydrogen, azido, cyano, formyl, halogen, OR$_{10}$, SR$_{11}$, COR$_{12}$, CR$_2$(=NOR$_4$) and CO$_2$R$_{13}$;

R$_{10}$ is selected from the group consisting of hydrogen, a C$_1$–C$_{10}$ alkyl group, a C$_3$–C$_{10}$ cycloalkyl group, an acyl radical of the type

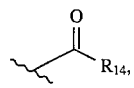

phenyl, benzyl and a 5–6 membered heteroaryl ring; said phenyl, benzyl and 5–6 membered heteroaryl ring being optionally substituted with one or more halogen, SCH$_3$, COOH, COOCH$_3$, OH, COOCH$_2$CH$_3$, OCH$_3$, OCH$_2$CH$_3$, NO$_2$, CF$_3$, C$_1$–C$_6$ alkyl, NH$_2$, and OAc;

R$_{14}$ is selected from the group consisting of methyl, ethyl, 1-(methyl)ethyl, n-propyl, tert-butyl, an alkyl radical of 4 to 10 carbon atoms, a cycloalkyl radical of 3 to 8 carbon atoms, phenyl, benzyl and a 5–6 membered ring heteroaryl radical; said phenyl, benzyl and a 5–6 membered ring heteroaryl radical being optionally substituted with one or more SCH$_3$, COOH, halogen, COOCH$_3$, COOCH$_2$CH$_3$, OH, OAc, OCH$_3$, OCH$_2$CH$_3$, NO$_2$, CF$_3$, C$_1$–C$_6$ alkyl and NH$_2$;

R$_{11}$ is selected from the group consisting of hydrogen, a C$_1$–C$_{10}$ alkyl group, a C$_3$–C$_{10}$ cycloalkyl group, an acyl radical of the type

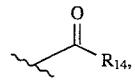

phenyl, benzyl and a 5–6 membered heteroaryl ring; said phenyl, benzyl and 5–6 membered heteroaryl ring being optionally substituted with one or more halogen, SCH$_3$, COOH, COOCH$_3$, COOCH$_2$CH$_3$, OH, OAc, OCH$_3$, OCH$_2$CH$_3$, NO$_2$, CF$_3$, C$_1$–C$_6$ alkyl and NH$_2$;

R$_{12}$ is selected from the group consisting of methyl, ethyl, 1-(methyl)ethyl; n-propyl, an alkyl radical of 4 to 10 carbon atoms, a C$_3$–C$_8$ cycloalkyl group, phenyl and benzyl; said phenyl and benzyl groups being optionally substituted with one or more SCH$_3$, COOH, COOCH$_3$, COOCH$_2$CH$_3$, OH, OAc, OCH$_3$, OCH$_2$CH$_3$, NO$_2$, CF$_3$, C$_1$–C$_6$ alkyl and NH$_2$, halogen; and R$_{13}$ is selected from the group consisting of hydrogen, methyl, ethyl, 1 -(methyl)ethyl, n-propyl, an alkyl radical of 4 to 10 carbon atoms, a C$_3$–C$_8$ cycloalkyl group, phenyl and benzyl; said phenyl and benzyl groups being optionally substituted with one or more halogen, SCH$_3$, COOH, COOCH$_3$, COOCH$_2$CH$_3$, OH, OAc, OCH$_3$, OCH$_2$CH$_3$, NO$_2$, NH$_2$, CF$_3$ and C$_1$–C$_6$ alkyl;

with the proviso that when m=0, R$_5$ is selected from the group consisting of cyano, formyl, COR$_{12}$, CO$_2$R$_{13}$ and CR$_2$(=NOR$_4$), G$_3$ is selected from the group consisting of cyano, —CHO, —COOR$_8$ and CR$_1$(=NOR$_3$);

R$_8$ is selected from the group consisting of hydrogen, methyl, ethyl, propyl, isopropyl and a C3–C6 alkyl group;

R$_1$ is selected from the group consisting of hydrogen, —OH, a C$_1$–C$_{10}$ alkyl group, a C$_2$–C$_{10}$ alkenyl group and a C$_2$–C$_{10}$ alkynyl group; said alkyl, alkenyl or alkynyl groups being optionally substituted with one or more groups selected from the group consisting of C$_1$–C$_6$ alkyl and phenyl;

R$_3$ is selected from the group consisting of hydrogen, a C$_1$–C$_{10}$ alkyl group, a C$_2$–C$_{10}$ alkenyl group, a C$_2$–C$_{10}$ alkynyl group, phenyl, benzyl and a heteroaromatic radical of the type:

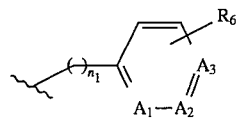

said $C_1$-$C_{10}$ alkyl, $C_2$-$C_{10}$ alkenyl, $C_2$-$C_{10}$ alkynyl, phenyl and benzyl groups being optionally substituted with one or more groups selected from the group consisting of $C_1$-$C_6$ alkyl and phenyl;

$A_1$, $A_2$, and $A_3$ are independently N, or C—H;

$R_6$ is selected from the group consisting of hydrogen, —OH, halogen, —$OCH_3$, —SH, —$S(O)n_2CH_3$, and —$NH_2$;

$n_1$=0–2; and $n_2$=0–2;

wherein $R_2$ is selected from the group consisting of hydrogen, —OH, a $C_1$-$C_{10}$ alkyl group, a $C_2$-$C_{10}$ alkenyl group and a $C_2$-$C_{10}$ alkynyl group; said alkyl, alkenyl or alkynyl groups being optionally substituted with one or more groups selected from the group consisting of $C_1$-$C_6$ alkyl and phenyl;

$R_4$ is selected from the group consisting of hydrogen, a $C_1$-$C_{10}$ alkyl group, a $C_2$-$C_{10}$ alkenyl group, a $C_2$-$C_{10}$ alkynyl group, phenyl, benzyl and a heteroaromatic radical of the type:

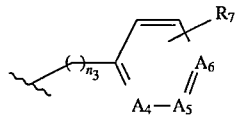

said $C_1$-$C_{10}$ alkyl, $C_2$-$C_{10}$ alkenyl, $C_2$-$C_{10}$ alkynyl, phenyl and benzyl groups being optionally substituted with one or more groups selected from the group consisting of $C_1$-$C_6$ alkyl and phenyl;

$A_4$, $A_5$, and $A_6$ are independently N, or C—H;

$R_7$ is selected from the group consisting of hydrogen, —OH, halogen, —$OCH_3$, —SH, —$S(O)n_4CH_3$, and —$NH_2$; and $n_3$=0–2; and $n_4$=0–2.

7. A compound of formula VII:

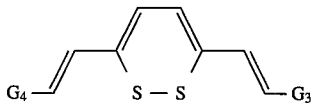

VII and pharmaceutically acceptable salts thereof, wherein:

$G_3$ is selected from the group consisting of cyano, —CHO, —$COOR_8$ and $CR_1$(=$NOR_3$);

$R_8$ is selected from the group consisting of hydrogen, methyl, ethyl, propyl, isopropyl and a C3–C6 alkyl group;

$R_1$ is selected from the group consisting of hydrogen, —OH, a $C_1$-$C_{10}$ alkyl group, a $C_2$-$C_{10}$ alkenyl group and a $C_2$-$C_{10}$ alkynyl group; said alkyl, alkenyl or alkynyl groups being optionally substituted with one or more groups selected from the group consisting of $C_1$-$C_6$ alkyl and phenyl;

$R_3$ is selected from the group consisting of hydrogen, a $C_1$-$C_{10}$ alkyl group, a $C_2$-$C_{10}$ alkenyl group, a $C_2$-$C_{10}$ alkynyl group, phenyl, benzyl and a heteroaromatic radical of the type:

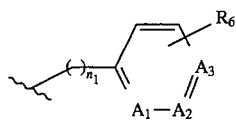

said $C_1$-$C_{10}$ alkyl, $C_2$-$C_{10}$ alkenyl, $C_2$-$C_{10}$ alkynyl, phenyl and benzyl groups being optionally substituted with one or more groups selected from the group consisting of $C_1$-$C_6$ alkyl and phenyl;

$A_1$, $A_2$, and $A_3$ are independently N, or C—H;

$R_6$ is selected from the group consisting of hydrogen, —OH, halogen, —$OCH_3$, —SH, —$S(O)n_2CH_3$, and —$NH_2$; and $n_1$=0–2;

$n_2$=0–2;

$G_4$ is selected from the group consisting of cyano, —CHO, —$COOR_9$; and $CR_2$(=$NOR_4$);

$R_9$ is selected from the group consisting of hydrogen, methyl, ethyl, propyl, isopropyl and a C3–C6 alkyl group;

$R_2$ is selected from the group consisting of hydrogen, —OH, a $C_1$-$C_{10}$ alkyl group, a $C_2$-$C_{10}$ alkenyl group and a $C_2$-$C_{10}$ alkynyl group; said alkyl, alkenyl or alkynyl groups being optionally substituted with one or more groups selected from the group consisting of $C_1$-$C_6$ alkyl and phenyl;

$R_4$ is selected from the group consisting of hydrogen, a $C_1$-$C_{10}$ alkyl group, a $C_2$-$C_{10}$ alkenyl group, a $C_2$-$C_{10}$ alkynyl group, phenyl, benzyl and a heteroaromatic radical of the type:

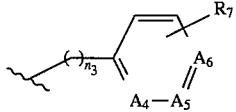

said $C_1$-$C_{10}$ alkyl, $C_2$-$C_{10}$ alkenyl, $C_2$-$C_{10}$ alkynyl, phenyl and benzyl groups being optionally substituted with one or more groups selected from the group consisting of C1–C6 alkyl and phenyl;

$A_4$, $A_5$, and $A_6$ are independently N, or C—H;

$R_7$ is selected from the group consisting of hydrogen, —OH, halogen, —$OCH_3$, —SH, —$S(O)n_4CH_3$, and —$NH_2$;

$n_3$=0–2; and $n_4$=0–2.

8. A compound of formula VIII:

VIII and pharmaceutically acceptable salts thereof, wherein:

$Z_1$ and $Z_2$ are independently selected from the group consisting of —$CH_2OH$, —CHO, —CH=CH—$CO_2A$, —CH=N—OB, —CH=CH—CN, and —CN;

A is selected from the group consisting of a $C_1$-$C_{10}$ alkyl group, a $C_2$-$C_{10}$ alkenyl group and a $C_2$-$C_{10}$ alkynyl group;

B is selected from the group consisting of hydrogen, a $C_1$-$C_{10}$ alkyl group, a $C_2$-$C_{10}$ alkenyl group and a $C_2$-$C_{10}$ alkynyl group; and with the proviso that $Z_1$ and $Z_2$ are not simultaneously —CHO, CN or —$CH_2OH$.

9. The compound of claim 8, selected from the group consisting of:

3-(Hydroxymethyl)-6-formyl-1,2-dithiin;

3-(hydroxymethyl)6-[ethyl propenoate-3-yl]-1,2-dithiin;

3-(hydroxymethyl)-6-[methyl propenoate-3-yl]-1,2-dithiin;

3-(hydroxymethyl)-6-[N-methoxyiminomethyl]-1,2-dithiin 3-(hydroxymethyl)-6-[N-hydroxyiminomethyl]-1,2-dithiin 3-(hydroxymethyl)-6-[2-cyanoethene-1-yl]-1,2-dithiin;

3-(hydroxymethyl)-6-cyano-1,2-dithiin;

3,6-[bis(N-hydroxyiminomethyl)]-1,2-dithiin; and 3,6-bis[N-methoxyiminomethyl]-1,2-dithiin.

10. A compound selected from the group consisting of:

3-[(tert-Butyldimethylsilyloxy)methyl]-6-formyl-1,2-dithiin;

3-[(tert-Butyldimethylsilyloxy)methyl]-6-[ethyl propenoate-3-yl]-1,2-dithiin;

3-[(tert-Butyldimethylsilyloxy)methyl]-6-[methyl propenoate-3-yl]-1,2-dithiin;

3-[(tert-Butyldimethylsilyloxy)methyl]-6-[N-methoxyiminomethyl]-1,2-dithiin;

3-[(tert-Butyldimethylsilyloxy)methyl]-6-[N-hydroxyiminomethyl]-1,2-dithiin;

3-[(tert-Butyldimethylsilyloxy)methyl]-6-[2-cyanoethene-1-yl]-1,2-dithiin; and

3-[(tert-Butyldimethylsilyloxy)methyl]-6-cyano-1,2-dithiin.

11. A method for inhibiting the growth of a pathogen, comprising contacting said pathogen with a compound according to claim 1, wherein said pathogen is selected from the group consisting of *Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, Histoplasma capsulatum, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdlovirus, Togavirus, Hepadnavirus, Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis, Streptococcus pyogenes; Straptococcus pneumonia, Viridans streptococci, Haemophilus influenzae, Proteus mirabilis, proteus vulgaris* and *Bacterioides fragilis.*

12. A method for inhibiting the growth of a pathogen, comprising contacting said pathogen with a compound according to claim 2, wherein said pathogen is selected from the group consisting of *Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, Histoplasma capsulatum, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdlovirus, Togavirus, Hepadnavirus, Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis, Streptococcus pyogenes; Straptococcus pneumonia, Viridans streptococci, Haemophilus influenzae, Proteus mirabilis, proteus vulgaris* and *Bacterioides fragilis.*

13. A method for inhibiting the growth of a pathogen, comprising contacting said pathogen with a compound according to claim 3, wherein said pathogen is selected from the group consisting of *Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, Histoplasma capsulatum, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdlovirus, Togavirus, Hepadnavirus, Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis, Streptococcus pyogenes; Straptococcus pneumonia, Viridans streptococci, Haemophilus influenzae, Proteus mirabilis, proteus vulgaris* and *Bacterioides fragilis.*

14. A method for inhibiting the growth of a pathogen, comprising contacting said pathogen with a compound according to claim 4, wherein said pathogen is selected from the group consisting of *Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, Histoplasma capsulatum, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdlovirus, Togavirus, Hepadnavirus, Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis, Streptococcus pyogenes; Straptococcus pneumonia, Viridans streptococci, Haemophilus influenzae, Proteus mirabilis, proteus vulgaris* and *Bacterioides fragilis.*

15. A method for inhibiting the growth of a pathogen, comprising contacting said pathogen with a compound according to claim 5, wherein said pathogen is selected from the group consisting of *Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, Histoplasma capsulatum, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdlovirus, Togavirus, Hepadnavirus, Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis,*

Streptococcus pyogenes; Straptococcus pneumonia, Viridans streptococci, Haemophilus influenzae, Proteus mirabilis, proteus vulgaris and Bacterioides fragilis.

16. A method for inhibiting the growth of a pathogen, comprising contacting said pathogen with a compound according to claim 6, wherein said pathogen is selected from the group consisting of Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, Histoplasma capsulatum, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdlovirus, Togavirus, Hepadnavirus, Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis, Streptococcus pyogenes; Straptococcus pneumonia, Viridans streptococci, Haemophilus influenzae, Proteus mirabilis, proteus vulgaris and Bacterioides fragilis.

17. A method for inhibiting the growth of a pathogen, comprising contacting said pathogen with a compound according to claim 7, wherein said pathogen is selected from the group consisting of Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, Histoplasma capsulatum, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdlovirus, Togavirus, Hepadnavirus, Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis, Streptococcus pyogenes; Straptococcus pneumonia, Viridans streptococci, Haemophilus influenzae, Proteus mirabilis, proteus vulgaris and Bacterioides fragilis.

18. A method for inhibiting the growth of a pathogen, comprising contacting said pathogen with a compound according to claim 8, wherein said pathogen is selected from the group consisting of Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, Histoplasma capsulatum, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdlovirus, Togavirus, Hepadnavirus, Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis, Streptococcus pyogenes; Straptococcus pneumonia, Viridans streptococci, Haemophilus influenzae, Proteus mirabilis, proteus vulgaris and Bacterioides fragilis.

19. A method for inhibiting the growth of a pathogen, comprising contacting said pathogen with a compound according to claim 9, wherein said pathogen is selected from the group consisting of Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, Histoplasma capsulatum, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdlovirus, Togavirus, Hepadnavirus, Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis, Streptococcus pyogenes; Straptococcus pneumonia, Viridans streptococci, Haemophilus influenzae, Proteus mirabilis, proteus vulgaris and Bacterioides fragilis.

20. A pharmaceutical composition for use as an agent to inhibit the growth of a pathogen in warm-blooded animals, comprising a therapeutically effective amount of a compound of claim 1.

21. A pharmaceutical composition for use as an agent to inhibit the growth of a pathogen in warm-blooded animals, comprising a therapeutically effective amount of a compound of claim 2.

22. A pharmaceutical composition for use as an agent to inhibit the growth of a pathogen in warm-blooded animals, comprising a therapeutically effective amount of a compound of claim 3.

23. A pharmaceutical composition for use as an agent to inhibit the growth of a pathogen in warm-blooded animals, comprising a therapeutically effective amount of a compound of claim 4.

24. A pharmaceutical composition for use as an agent to inhibit the growth of a pathogen in warm-blooded animals, comprising a therapeutically effective amount of a compound of claim 5.

25. A pharmaceutical composition for use as an agent to inhibit the growth of a pathogen in warm-blooded animals, comprising a therapeutically effective amount of a compound of claim 6.

26. A pharmaceutical composition for use as an agent to inhibit the growth of a pathogen in warm-blooded animals, comprising a therapeutically effective amount of a compound of claim 7.

27. A pharmaceutical composition for use as an agent to inhibit the growth of a pathogen in warm-blooded animals, comprising a therapeutically effective amount of a compound of claim 8.

28. A pharmaceutical composition for use as an agent to inhibit the growth of a pathogen in warm-blooded animals, comprising a therapeutically effective amount of a compound of claim 9.

* * * * *